US012635858B2

(12) United States Patent

Chu et al.

(10) Patent No.: US 12,635,858 B2
(45) Date of Patent: May 26, 2026

(54) ATTACHMENT SYSTEM FOR ENDOSCOPES

(71) Applicant: 9393-2655 QUEBEC INC., Montreal (CA)

(72) Inventors: Boby Chu, Lasalle (CA); Bruno Chabot, Montreal (CA); Benoit Thibault, Coteau-du-Lac (CA); Teresa Mihalik, Montreal (CA)

(73) Assignee: ENDOCISION TECHNOLOGIES INC., Montreal (CA)

( * ) Notice: Subject to any disclaimer, the term of this patent is extended or adjusted under 35 U.S.C. 154(b) by 510 days.

(21) Appl. No.: 17/924,774

(22) PCT Filed: May 12, 2021

(86) PCT No.: PCT/CA2021/050658
§ 371 (c)(1),
(2) Date: Nov. 11, 2022

(87) PCT Pub. No.: WO2021/226715
PCT Pub. Date: Nov. 18, 2021

(65) Prior Publication Data

US 2023/0172436 A1     Jun. 8, 2023

Related U.S. Application Data

(60) Provisional application No. 63/024,030, filed on May 13, 2020.

(51) Int. Cl.
*A61B 1/00*          (2006.01)
(52) U.S. Cl.
CPC ........ *A61B 1/0014* (2013.01); *A61B 1/00135* (2013.01)

(58) Field of Classification Search
CPC .. A61B 1/0014; A61B 1/00135; A61B 1/0011
See application file for complete search history.

(56) References Cited

U.S. PATENT DOCUMENTS 5,259,366 A     11/1993 Reydel et al.
5,489,256 A *    2/1996 Adair ................. A61B 1/00101
                                                              600/156

(Continued)

FOREIGN PATENT DOCUMENTS

CN          209285449 U      8/2019
JP          2008506459 A     3/2008
JP          2011507660 A     3/2011

(Continued)

OTHER PUBLICATIONS

Supplementary European Search Report issued in co-pending European patent application No. 21804813.0 on May 2, 2024.

(Continued)

*Primary Examiner* — Timothy J Neal
(74) *Attorney, Agent, or Firm* — BCF LLP

(57)          ABSTRACT

An attachment system for detachably attaching an additional channel to an endoscope, the attachment system comprising: a sleeve for receiving a distal end of the endoscope and a distal end of the additional channel in use, the sleeve having: a sleeve body defining a sleeve channel, through which the distal end of the endoscope and the distal end of the additional channel will extend in use, and having a first open end and a second open end; a rupture mechanism for rupturing the sleeve body to allow separation of the distal end of the additional channel from the distal end of the endoscope.

20 Claims, 13 Drawing Sheets

(56) References Cited

U.S. PATENT DOCUMENTS

| | | | |
|---|---|---|---|
| 2004/0092892 A1* | 5/2004 | Kagan ................. | A61B 17/0401 |
| | | | 604/270 |
| 2005/0080405 A1* | 4/2005 | Bischof .................. | A61B 18/02 |
| | | | 606/20 |
| 2005/0159645 A1* | 7/2005 | Bertolero ........... | A61B 1/00142 |
| | | | 600/116 |
| 2006/0015171 A1* | 1/2006 | Armstrong ....... | A61B 17/12172 |
| | | | 623/1.12 |
| 2006/0063972 A1* | 3/2006 | Chang ...................... | A61B 1/31 |
| | | | 600/114 |
| 2010/0063359 A1* | 3/2010 | Okoniewski ....... | A61B 1/00142 |
| | | | 600/121 |
| 2011/0313242 A1 | 12/2011 | Surti | |
| 2013/0022599 A1 | 1/2013 | Hart et al. | |
| 2016/0081537 A1 | 3/2016 | Farhadi | |
| 2016/0324412 A1* | 11/2016 | Hassidov ................. | A61B 1/31 |

FOREIGN PATENT DOCUMENTS

| | | |
|---|---|---|
| JP | 2020508086 A | 3/2020 |
| WO | 2015193896 A1 | 12/2015 |

OTHER PUBLICATIONS

Kong, M-S. et al, Home-made double-channel endoscope for pediatric patients, Journal of the Formosan Medical Association, vol. 106, Issue 4, pp. 336-338, Jan. 31, 2007.
International Search Report and Written Opinion issued in corresponding International application No. PCT/CA2021/050658 on Aug. 9, 2021.

* cited by examiner

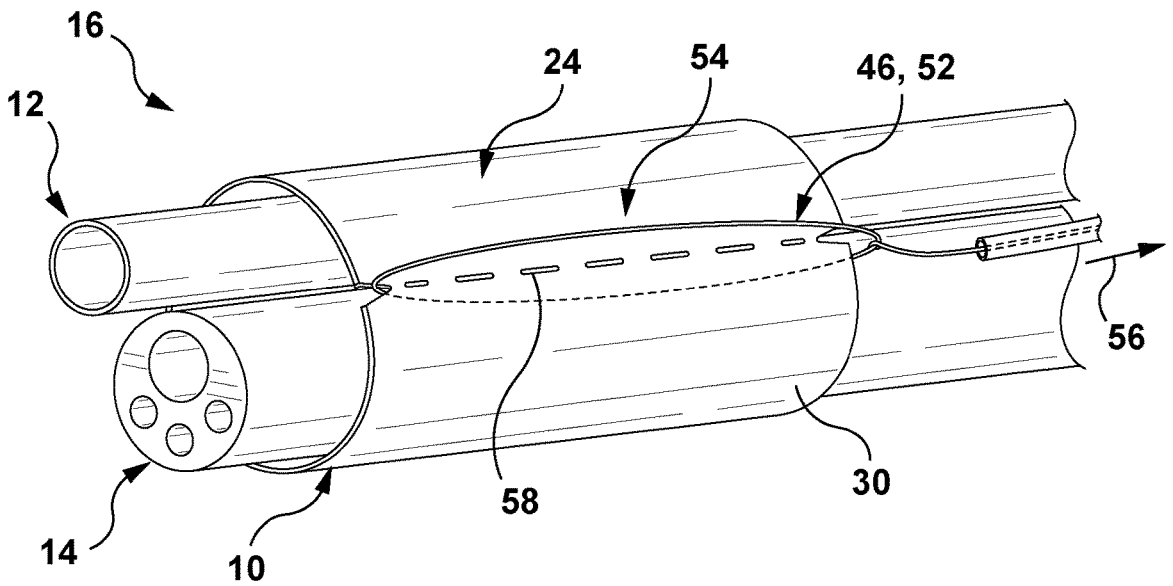
FIG. 4
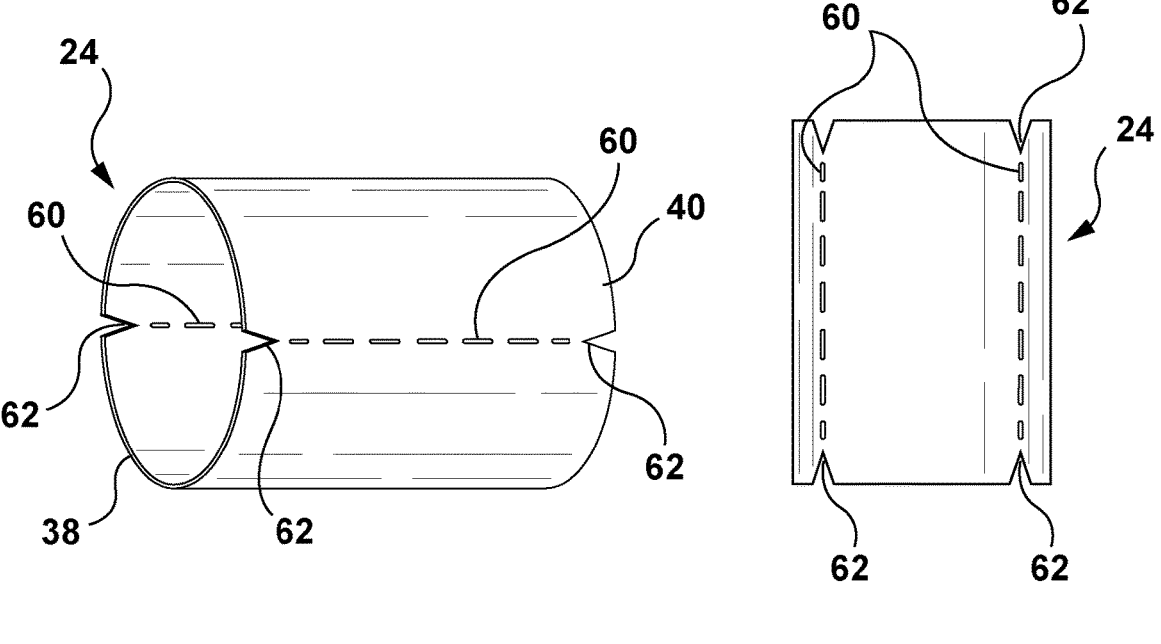
FIG. 5A                    FIG. 5B

194

166

14

12

192

188

190

ATTACHMENT SYSTEM FOR ENDOSCOPES

FIELD OF THE DISCLOSURE

The present disclosure relates to an attachment system for endoscopes, more specifically but not exclusively to an attachment system for endoscopes for detachably attaching an additional working channel thereto.

BACKGROUND OF THE DISCLOSURE

Endoscopes are medical devices used to access a patient's target anatomy for diagnostic or therapeutic purposes. Endoscopes typically comprise an elongate body having a distal end which can be inserted into the patient's anatomy. The elongate body typically has one or more working channels (also referred to as "native working channels") for enabling passage of functional instruments such as balloons, forceps, catheters, scissors, suction apparatus, optical fibers, and cameras, as well as for transmitting light and permitting visualization. Different types of endoscopes include bronchoscopes, gastroscopes, colonoscopes, and the like.

In certain situations, it is desirable to provide one or more additional working channels in addition to the native working channels of the endoscope for additional functionality. It is also desirable, in certain situations, to be able to independently operate the additional working channel and the native working channels of the endoscope. One example of independently operating the additional working channel and the endoscope includes an ability to separate the additional working channel from the endoscope whilst both are in situ in the patient so that one of them remains in the patient whilst the other is removed.

Systems for attaching an additional working channel to an endoscope have been proposed but do not permit controllable separation from the endoscope in situ.

Therefore, there is a need for attachment systems for endoscopes which overcome or reduce at least some of the above-described problems.

SUMMARY OF THE DISCLOSURE

It is an object of the present disclosure to ameliorate at least some of the inconveniences present in the prior art.

According to certain aspects and embodiments of the present technology, at least one additional working channel may be attached to an endoscope which additional working channel can be separated from the endoscope in situ in the patient and operated independently. This can provide a clinician with more control during a procedure, translating to safer outcomes for the patient. The additional working channel is an external channel to the native working channel of the endoscope, and is referred to interchangeably as "additional channel".

Accordingly, by means of certain aspects and embodiments of the present technology, an attachment system is provided for releasably assembling together distal ends of an endoscope and an additional channel. The attachment system includes a sleeve for receiving the endoscope distal end and the additional channel distal end. A rupture mechanism is provided for rupturing the sleeve to allow separation of the endoscope distal end and the additional channel distal end whilst the sleeve is in situ in the patient. The rupture mechanism can be deployed from a proximal end of the endoscope, external to the patient, by a user of the attachment system.

From one aspect, there is provided an attachment system for detachably attaching an additional channel to an endoscope, the attachment system comprising: a sleeve for receiving a distal end of the endoscope and a distal end of the additional channel in use, the sleeve having: a sleeve body defining a sleeve channel, through which the distal end of the endoscope and the distal end of the additional channel will extend in use, and having a first open end and a second open end; a rupture mechanism for rupturing the sleeve body to allow separation of the distal end of the additional channel from the distal end of the endoscope. The rupture mechanism can be operated from outside the patient whilst the sleeve is in situ in the patient. This can allow separate operation of the additional channel and the endoscope.

In certain embodiments, the sleeve body is attached to the rupture mechanism.

In certain embodiments, the rupture mechanism can be deployed proximally to the sleeve.

In certain embodiments, the rupture mechanism comprises a blade mechanism which is arranged to cut the sleeve body between the first open end to the second open end when relative movement is imparted between the sleeve body and the blade mechanism, and a leash for imparting the relative movement between the sleeve body and the blade mechanism.

In certain embodiments, the blade mechanism comprises a blade mechanism body having a first arm joined to a second arm, and a blade positioned between the first arm and the second arm, wherein the first arm is arranged to extend along an outside of the sleeve body, and the second arm is arranged to extend along an inside of the sleeve body.

In certain embodiments, the blade mechanism is hooked over a distal edge of the sleeve body or a proximal edge of the sleeve body.

In certain embodiments, the leash is a sleeve leash and comprises a first end attached to the sleeve body, and a second end extending proximally from the first end and arranged to be actuated by a user to cause the sleeve body to move.

In certain embodiments, the first end of the sleeve leash comprises a looped portion extending around the sleeve body and through the sleeve channel. The second end may be attached to the blade mechanism body.

In certain embodiments, the leash is a blade leash and comprises a first end attached to the blade mechanism body, and a second end extending proximally from the first end and arranged to be actuated by a user to cause the blade mechanism body to move.

In certain embodiments, the rupture mechanism is a snare mechanism comprising a first end attached to the sleeve body, and a second end extending proximally from the first end and arranged to be actuated by a user to cause the sleeve body to rupture. The first end of the snare mechanism may comprise a looped portion extending around the sleeve body and through the sleeve channel.

In certain embodiments, the attachment mechanism further comprises a frangible portion on the sleeve body extending between the first open end and the second open end, the snare mechanism being arranged to contact the frangible portion when actuated to cause the frangible portion to rupture. The frangible portion may comprise perforations. The perforations may be arranged as a single row extending between the first open end and the second open end; or the perforations may be arranged as two rows, each row extending between the first open end and the second open end.

In certain embodiments, the attachment system further comprises a slit at a distal edge or at a proximal edge of the sleeve body, adjacent the perforations.

In certain embodiments, wherein the rupture mechanism is a removeable strip on the sleeve body, the removeable strip is defined by two rows of perforations on the sleeve body extending between the first open end and the second open end, the removeable strip being actuatable at one end to rupture the perforations to detach the removeable strip.

In certain embodiments, the rupture mechanism is a removeable strip on the sleeve body, the removeable strip defined by two rows of perforations on the sleeve body extending between the first open end and the second open end, the removeable strip being configured such that an actuation of the removeable strip can rupture at least some of the perforations to rupture the sleeve body to allow separation of the distal end of the additional channel from the distal end of the endoscope.

In certain embodiments, there is further provided a tab leash, connected at a first end to the one end of the removeable strip, and having a second end extending proximally from the first end and arranged to be actuatable to detach the removeable strip.

In certain embodiments, there is further provided a tab leash having a first end and a second end, the first end being connected to the removeable strip, wherein pulling the second end of the tab leash causes at least some of the perforations to rupture.

In certain embodiments, the first end of the tab leash is connected to the removeable strip by a tab. The tab may extend from one end of the removeable strip. A tether may be provided for connecting the detached removeable strip to the sleeve body. The tether may be attached at one end to the sleeve body and at the other end to the removeable strip.

In certain embodiments, the attachment system further comprises a tensioning mechanism for providing a tension to the sleeve. The tensioning mechanism comprises at least one pin having a hook portion and a hook arm extending from the hook portion, wherein the at least one pin is insertable into the sleeve with the hook arm extending along an outer surface of the sleeve body, and the hook portion extending over a distal edge of the sleeve body in use, or over a proximal edge of the sleeve body in use.

In certain embodiments, the at least one pin is attached to the additional channel. The additional channel may have a sheath defining a channel for hosting a guide wire for example, and the at least one pin is attached to the sheath.

In certain embodiments, the at least one pin comprises two pins attached to the additional channel and spaced circumferentially from one another. In use, with the additional channel, endoscope and attachment system assembled, the hook arm cinches the sleeve. In certain embodiments, the sleeve body is cinched along more than 50% of its length, for example along a 5-15 mm distance. Advantageously, the cinching ensures that the endoscope and the additional channel move together within the patient and can follow the endoscope's curve of deflection. In prior art systems which provide a thin loop or lasso type attachment of an endoscope and an additional channel, deflection of the endoscope will cause misalignment of the additional channel with the endoscope tip. This means that the prior art systems cannot be navigated along paths that are not straight (e.g. in an upper airway of a patient).

In certain embodiments, the tensioning mechanism comprises an adjustable portion on the sleeve body, which adjustable portion can be actuated to modulate (adapt) a cross-sectional area of the sleeve. The adjustable portion may extend longitudinally along the sleeve body and comprises a thread extending through the sleeve body which can be pulled to make the cross-sectional area of the sleeve smaller in certain embodiments.

In certain embodiments, the thread extends in a zig-zag configuration longitudinally along the sleeve body.

In certain embodiments, the sleeve body has a slit extending longitudinally between the first and second open ends of the sleeve body, the slit defined by a first slit edge and a second slit edge, the thread being arranged to extend alternately through the first slit edge and the second slit edge to bring closer together the first and second slit edges of the sleeve body.

In certain embodiments, the attachment system further comprises a plurality of loops extending from the first and second slit edges, each loop of the plurality of loops being arranged to receive the thread. In certain embodiments, the loops on the first slit edge are arranged in an inter-digitated configuration relative to the loops on the second slit edge.

In certain embodiments, the attachment system further comprises an anti-rotation device configured to hinder or limit non-axial movement between the additional channel and the endoscope. In some embodiments, the anti-rotation device may permit relative axial movement between the additional channel and the endoscope. The anti-rotation device may be removably attachable to one or both of the additional channel and the endoscope.

In certain embodiments, the anti-rotation device comprises a wing clip. The wing clip has a body arranged to clip around the additional channel or the endoscope, or to otherwise attach to the additional channel or the endoscope. The wing clip is arranged to limit or reduce a relative movement between the additional channel and the endoscope.

In certain embodiments, the body of the wing clip has a first open end and a second open end and defines a cylindrical channel through which the additional channel or the endoscope can extend. The body may be u-shaped. The body may have a side (longitudinal) opening facilitating the positioning of the wing clip around the additional channel or the endoscope. A pair of wings may extend from side opening edges, which define the side opening. The pair of wings may flare apart and define an area for receiving one or other of the additional channel or the endoscope. In embodiments in which the wing clip is attached to the additional channel, the pair of wings rest on an outer surface of the endoscope, and limit rotational movement between the additional channel and the endoscope.

In certain embodiments, the wing clip does not clip to the additional channel but is arranged to rest under the additional channel and attached thereto using for example adhesive or fusion. Accordingly the body of the wing clip may define a more shallow u-shape. With such embodiments, an overall dimension of the additional channel is not increased.

In certain embodiments, the attachment system further comprises the additional channel, the additional channel comprises a sheath sized and shaped to house a guide wire.

In certain embodiments, the additional channel further comprises a steering cable for independent positioning of the additional channel.

In certain embodiments, the attachment system further comprises the endoscope. The endoscope has a working channel permitting one or more of: visualization and suction, in certain embodiments.

In certain embodiments, the endoscope is a bronchoscope.

From another aspect, there is provided an attachment system for detachably attaching an additional channel to an endoscope, the attachment system comprising: a sleeve for receiving a distal end of the endoscope and a distal end of the additional channel in use, the sleeve having: a sleeve body defining a sleeve channel, through which the distal end of the endoscope and the distal end of the additional channel will extend in use, and having a first open end and a second open end; a rupture mechanism for rupturing the sleeve body to allow separation of the distal end of the additional channel from the distal end of the endoscope, the rupture mechanism comprising a removeable strip, the removeable strip defined by two rows of perforations on the sleeve body extending between the first open end and the second open end, the removeable strip being actuatable at one end to rupture the perforations to detach the removeable strip, and a tensioning mechanism comprising an adjustable portion on the sleeve body, which adjustable portion can be actuated to modulate a cross-sectional area of the sleeve body.

In certain embodiments, the adjustable portion extends longitudinally along the sleeve body and comprises a thread extending through the sleeve body which can be pulled to make the cross-sectional area of the sleeve body smaller.

In certain embodiments, the thread extends in a zig-zag configuration longitudinally along the sleeve body.

In certain embodiments, the sleeve body has a slit extending longitudinally between the first and second open ends of the sleeve body, the slit defined by a first slit edge and a second slit edge, the thread being arranged to extend alternately through the first slit edge and the second slit edge to bring closer together the first and second slit edges of the sleeve body when actuated.

In certain embodiments, the attachment system further comprises a plurality of loops extending from the first and second slit edges, each loop of the plurality of loops being arranged to receive the thread.

In certain embodiments, the loops on the first slit edge are arranged in an inter-digitated configuration relative to the loops on the second slit edge.

In certain embodiments, the removeable strip further comprises a tab leash, connected at a first end to the one end of the removeable strip, and having a second end extending proximally from the first end and arranged to be actuatable to pull the removeable strip to rupture the perforations.

In certain embodiments, the removeable strip further comprises a tab leash having a first end and a second end, the first end connected to the removeable strip, wherein pulling the second end causes at least some of the perforations to rupture.

In certain embodiments, the attachment system further comprises a tab extending from the one end of the removeable strip, the first end of the tab leash being attached to the tab. In certain embodiments, the tab leash is connected to the removeable strip by a tab.

In certain embodiments, the attachment system further comprises a tether for connecting the detached removeable strip to the sleeve. The tether may be connected at one end to the removeable strip and at another end to the sleeve body.

From a yet further aspect, there is provided a kit comprising the attachment system, according to any of the embodiments described herein, and the additional channel as described herein.

In certain embodiments, the attachment system comprises: a sleeve for receiving a distal end of the endoscope and a distal end of the additional channel in use, the sleeve having: a sleeve body defining a sleeve channel, through which the distal end of the endoscope and the distal end of the additional channel will extend in use, and having a first open end and a second open end; a rupture mechanism for rupturing the sleeve body to allow separation of the distal end of the additional channel from the distal end of the endoscope, the rupture mechanism comprising a removeable strip portion of the sleeve body the removal of which ruptures the sleeve body. The removeable strip can be removed by pulling on a tab leash attached to the removable strip portion. The removable strip may be tethered to the sleeve by a tether so that it remains attached to the sleeve even after the sleeve body has been ruptured. The tab leash may have a handle attached thereto for actuation by a user. In certain embodiments, the attachment system comprises a tensioning mechanism which is a thread strung through the sleeve body. Pulling the thread can make the cross-sectional area of the sleeve body smaller. The thread may have one or two handles attached to one or both ends for actuation by the user. The sleeve body and the handles may be removably mounted to a packaging, such as a cardboard backing.

In certain embodiments, the kit further comprises the endoscope.

In certain embodiments, the additional channel comprises a sheath sized and shaped to house a guide wire.

In certain embodiments, the kit further comprises a biopsy device. In certain embodiments, the biopsy device comprises a cryobiopsy device.

In certain embodiments, the kit further comprises an anti-rotation device which can be releasably attachable to the additional channel and/or the endoscope and configured to prevent or limit an undesired relative movement of the additional channel and/or the endoscope. The undesired relative movement may be a relative rolling of one against the other. The anti-rotation device is a wing clip in certain embodiments.

From another aspect, there is provided an attachment system for detachably attaching an additional channel to an endoscope, the attachment system comprising: a sleeve for receiving a distal end of the endoscope and a distal end of the additional channel in use, the sleeve having: a sleeve body defining a sleeve channel, through which the distal end of the endoscope and the distal end of the additional channel will extend in use, and having a first open end and a second open end; a tensioning mechanism comprising an adjustable portion on the sleeve body, which adjustable portion can be actuated to modulate a cross-sectional area of the sleeve body.

In certain embodiments, the adjustable portion extends longitudinally along the sleeve body and comprises a thread extending through the sleeve body which can be pulled to make the cross-sectional area of the sleeve body smaller.

In certain embodiments, the thread extends in a zig-zag configuration longitudinally along the sleeve body.

In certain embodiments, the sleeve body has a slit extending longitudinally between the first and second open ends of the sleeve body, the slit defined by a first slit edge and a second slit edge, the thread being arranged to extend alternately through the first slit edge and the second slit edge to bring closer together the first and second slit edges of the sleeve body when actuated.

In certain embodiments, the attachment system further comprises a plurality of loops extending from the first and second slit edges, each loop of the plurality of loops being arranged to receive the thread.

In certain embodiments, the loops on the first slit edge are arranged in an inter-digitated configuration relative to the loops on the second slit edge.

In certain embodiments, the removeable strip further comprises a tab leash, connected at a first end to the one end of the removeable strip, and having a second end extending proximally from the first end and arranged to be actuatable to pull the removeable strip to rupture the perforations.

In certain embodiments, the removeable strip further comprises a tab leash having a first end and a second end, the first end connected to the removeable strip, wherein pulling the second end can cause at least some of the perforations to rupture.

In certain embodiments, the attachment system further comprises a tab extending from the one end of the removeable strip, the first end of the tab leash being attached to the tab. In certain embodiments, the tab leash is connected to the removeable strip by a tab.

In certain embodiments, the attachment system further comprises a tether for connecting the detached removeable strip to the sleeve.

In certain embodiments, the tensioning mechanism comprises at least one pin having a hook portion and a hook arm extending from the hook portion, wherein the at least one pin is insertable into the sleeve body with the hook arm extending along an outer surface of the sleeve body, and the hook portion extending over a distal edge of the sleeve body in use, or over a proximal edge of the sleeve body in use.

In certain embodiments, the at least one pin is attached to the additional channel or to the endoscope. In certain embodiments, the at least one pin comprises two pins attached to the additional channel or to the endoscope and spaced circumferentially from one another.

From a yet further aspect, there is provided a method for performing a biopsy, the method comprising, positioning the assembly of the sleeve, the endoscope and the additional channel in a target tissue site of a patient, deploying the rupture mechanism to separate the endoscope and the additional channel, and removing one of the endoscope and the additional channel whilst the other of the endoscope and the additional channel remains at the target tissue site.

From a yet further aspect, there is provided a method for removeably assembling an endoscope with an additional channel, the method comprising surrounding the distal end of the endoscope and the distal end of the additional channel with the attachment system as defined herein.

From another aspect, there is provided an attachment system for attaching together a distal end of an endoscope and a distal end of an additional channel comprising a sleeve, and including a tensioning system for modifying a cross-sectional area of the sleeve.

From yet another aspect, there is provided a kit comprising the attachment system for endoscopes described above, and an additional channel system. The additional channel system can include one or more tools which can be delivered and removed via a sheath of the additional channel. In certain embodiments, the kit is a biopsy kit and the additional channel system comprises a biopsy system. The biopsy system can include a biopsy device (such as a cryogenic catheter or probe), and optionally a balloon occlusion device.

In certain embodiments, aspects and embodiments of the present technology can be used during a lung biopsy procedure. In these embodiments, the endoscope is a bronchoscope.

A lung biopsy procedure requires forceps or cryobiopsy device for removing lung tissue, a deployable balloon occlusion device to control bleeding post-biopsy, and a lit working channel for visualization of the airways during the biopsy as well as during the deployment of the balloon. Developers have noted certain shortcomings with a typical lung biopsy procedure. The balloon occlusion device must first be delivered into the lung space for bleeding control post-biopsy. Currently, in order to accomplish this, a guide wire is first delivered to the target airway in the lung space through a bronchoscope working channel, after which the bronchoscope must be completely removed from the lung to free the guide wire and to allow the balloon occlusion device to be loaded over the guide wire. This causes loss of airway visualization during that time. The balloon occlusion device is left deflated for use later on in the procedure.

The bronchoscope is then repositioned in the patient's airway adjacent the guide wire with the non-deployed balloon occlusion device. To enable the tissue biopsy, a biopsy device (e.g. forceps device, cryobiopsy device, etc) is inserted into the native working channel of the bronchoscope and the biopsy device and the bronchoscope are navigated together using the deflection/steering mechanism of the bronchoscope to the target biopsy site. The presence of the biopsy probe inside the working channel of the bronchoscope may adversely affect the suction performance as biopsy devices are approximately 2 mm in width, which is approximately equivalent to the working channel of the bronchoscope. This may cause discomfort to the patient and may affect the operator's ability to properly visualize the biopsy process.

For taking a frozen biopsy, a freezing cycle (approximately between about 5-10 s) is initiated with a cryogenic delivery system, which causes a sample of tissue to freeze and be attached to a cryogenic probe tip of the biopsy device. The frozen tissue sample attached to the probe tip of the biopsy device tip is extracted from the lung biopsy site by pulling the probe tip of the biopsy device away from the lung biopsy site. The alternative to cryobiopsy is biopsy with forceps.

During extraction of the frozen tissue sample, the balloon device is deployed once the probe tip with the adhered tissue sample is proximal to the balloon. The deployed balloon creates a barrier for any bleeding that may have occurred during tissue sample extraction and to mitigate the safety risk of any blood migrating into the lung passages and causing asphyxiation. The balloon is typically left deployed for approximately 5 minutes.

The tissue sample is typically larger than the bronchoscope working channel, thus the only way to remove the tissue sample without crushing, damaging, or losing it is by removing the bronchoscope and biopsy device together. This means that the operator no longer has visual control of the airway and is not able to monitor whether bleeding has occurred, whether the deployed balloon is in the correct position, and the severity of any bleeding.

According to guidelines for lung biopsy, three to five biopsies are recommended from multiple locations within the lung for increasing diagnostic certainty, and even from multiple lobes. For subsequent biopsies, the bronchoscope must be repositioned back to the initial position and the process repeated for the subsequent tissue samples.

If a biopsy is desired in a different location, the entire procedure including initial placement of the guide wire and balloon occlusion device must be repeated. In the case of five biopsies in five different locations, the bronchoscope can be inserted and removed up to ten times from the lung (five times to place the bleeding control balloon, and five times to retrieve tissue specimens). Further, additional insertion/removal cycles may be needed as in about 30% of cases, the retrieved tissue specimen is damaged or has fallen from the biopsy device.

By means of aspects and embodiments of the present technology, the endoscope is a bronchoscope and the additional channel includes a guide wire for advancing a balloon occlusion device and a biopsy device. In certain embodiments, the guide wire can be preloaded with the balloon occlusion device before attachment of the additional channel to the bronchoscope with the sleeve of the attachment system, and before insertion into the patient. In this way, the bronchoscope and the balloon occlusion device with preloaded guidewire, connected by the attachment system can be delivered together to the target site. In use, once the balloon occlusion device is in the correct position in the lung of the patient, the sleeve can be ruptured to separate the balloon occlusion device from the bronchoscope.

This represents a significant improvement over prior art systems in which the guide wire is first delivered to the target site in the patient through the native working channel of the bronchoscope. The guide wire is then freed by removing the bronchoscope completely from the lung, losing visual control of the lung airways, followed by loading the balloon occlusion device over the guide wire. Loading the balloon catheter over the guide wire whilst the guide wire is in the patient is a difficult and cumbersome process for the clinician as the clinician must support the bronchoscope, which is relatively heavy, whilst maintaining the guide wire in position in the patient's lung and positioning the occlusion device over the guide wire. As the patient is in a reclined seated position, the instrumentation must be held by the clinician relative to the patient's position. It is not uncommon for the guide wire to slip out of position in the patient's lung during the loading process.

The sleeve of the system connects together the distal end of the additional channel and the distal end of the bronchoscope, and the rupture mechanism permits in situ separation of the same. The assembled bronchoscope and additional channel are positioned in the patient's airway together, and the rupture mechanism can permit separation of the bronchoscope and the additional channel in situ in the patient.

By means of the attachment system, the biopsy device can be removed independently from the bronchoscope. During that time, the operator is able to continuously visualize the airway using the bronchoscope, assess the presence or severity of bleeding and whether the balloon occlusion device is appropriately deployed and effective for bleeding control.

Advantages of the present technology include one or more of: an ability to maintain visual control of airways during insertion of balloon occlusion device; maintain visual control of airways during cryobiopsy tissue retrieval; enable airway management via fluid suctioning through bronchoscope working channel; minimize bronchoscope insertions and withdrawals into lung; and maintain or improve safety profile and efficacy of current cryobiopsy procedures.

The operator may be a clinician or clinical practitioner such as a pulmonologist, a thoracic surgeon, an endoscopist, an intensive/critical care physician, a radiologist, or the like.

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each is set out individually herein.

These and other aspects and features of non-limiting embodiments will now become apparent to those skilled in the art upon review of the following description of specific non-limiting embodiments in conjunction with the accompanying drawings.

BRIEF DESCRIPTION OF DRAWINGS

Further aspects and advantages of the present invention will become better understood with reference to the description in association with the following in which:

FIG. 4 is a perspective view from the side of an attachment system with an alternative sleeve, according to certain other embodiments of the present technology;

FIGS. 5A and 5B are perspective and top views, respectively, of the sleeve of FIG. 4, according to certain other embodiments of the present technology;

Figures 1, 2, 3:
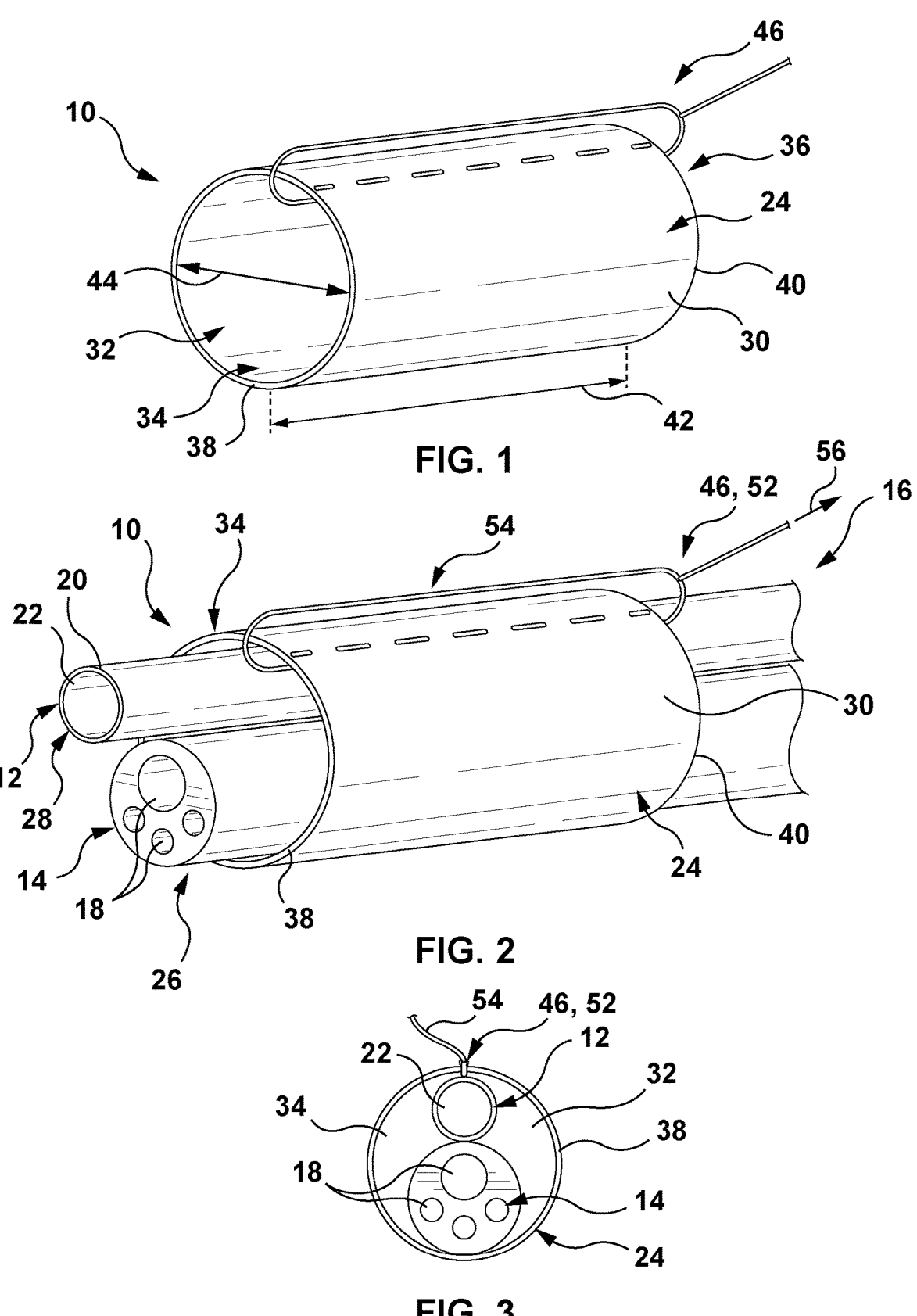
FIG. 1 is a perspective view of an attachment system including a sleeve and a rupture mechanism which is a snare mechanism, according to certain embodiments of the present technology.
FIG. 2 is a perspective view of the attachment system of FIG. 1 assembled with an endoscope and an additional channel, according to certain embodiments of the present technology.
FIG. 3 is an end view of the attachment system of FIG. 2, according to certain embodiments of the present technology.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Reference will now be made in detail to various non-limiting embodiments of attachment systems for endoscopes. It should be understood that other non-limiting embodiments, modifications and equivalents will be evident to one of ordinary skill in the art in view of the non-limiting embodiments disclosed herein and that these variants should be within scope of the appended claims.

Furthermore, it will be recognized by one of ordinary skill in the art that certain structural and operational details of the non-limiting embodiments discussed hereafter may be modified or omitted (i.e. non-essential) altogether. In other instances, well known methods, procedures, and components have not been described in detail.

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

Broadly, there is provided an attachment system 10 for detachably attaching an additional channel 12 to an endoscope 14 to provide an assembly 16 comprising the endoscope 14 and the additional channel 12. The additional channel 12 can be considered as supplementary to the native working channels 18 of the endoscope and external thereto. The assembly 16 can be inserted to a target position inside a patient to perform various functions through the additional channel 12 and the native working channels 18 of the endoscope 14. The attachment system 10 allows the insertion of both the endoscope 14 and the additional channel 12 together, attached as the assembly 16. The attachment system 10 also allows detachment of the endoscope 14 and the additional channel 12 such that one can be removed from the target position whilst the other remains in the target position. The detachment of the additional channel 12 from the endoscope 14 can be controllably deployed by a user of the attachment system 10 from outside of the patient. In certain embodiments, the additional channel 12 comprises a sheath 20 defining the additional channel 12. It will be appreciated that embodiments of the attachment system 10 can be used with any type of additional channel 12 and any type of endoscope 14. The additional channel 12 and the endoscope can be used to deliver any type of device.

Figures 16A, 16B:
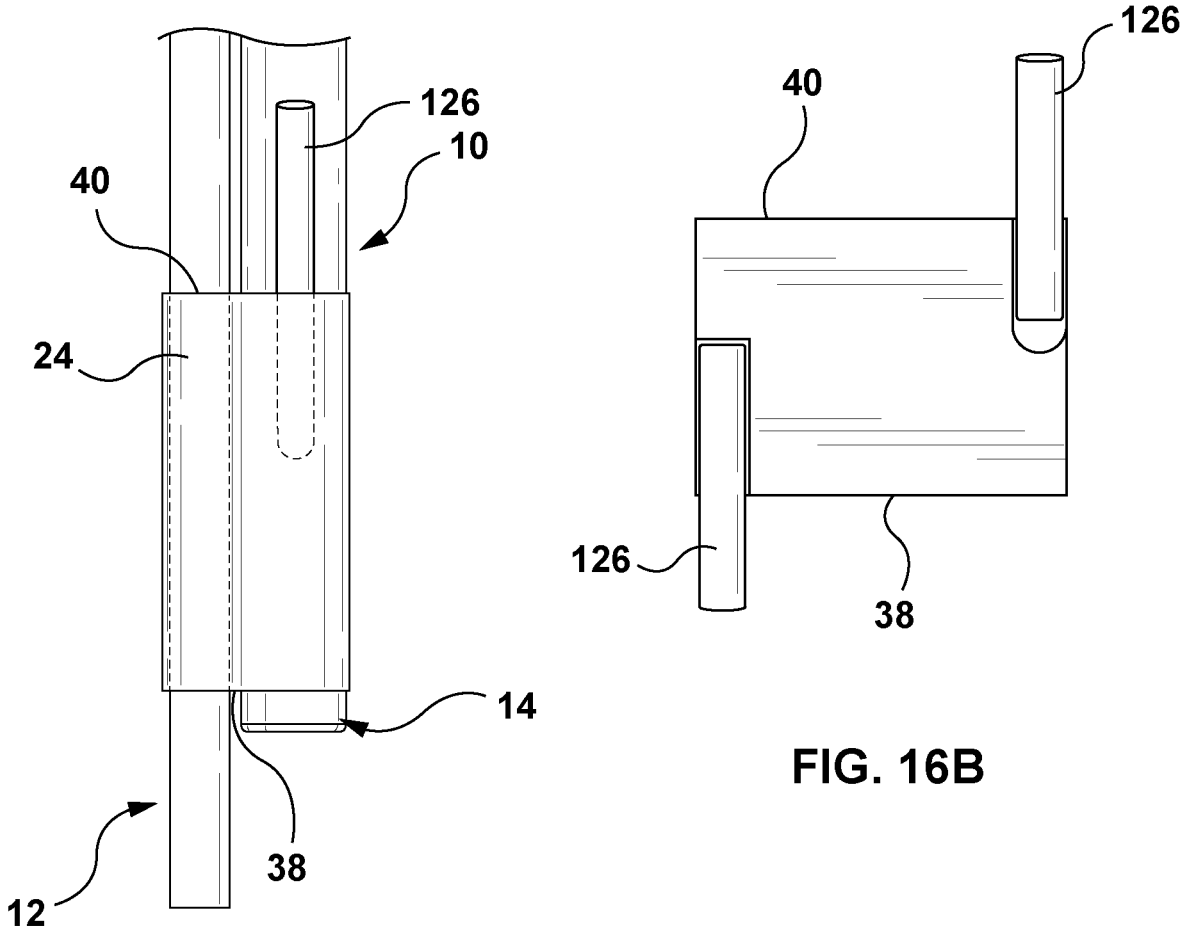
FIG. 16A is a perspective view of an attachment system including an alternative sleeve, according to certain other embodiments of the present technology.
FIG. 16B is plan view of a sleeve of the attachment system of FIG. 16A when opened up, according to certain embodiments of the present technology.

Referring to FIGS. 1-14, the attachment system 10 comprises a sleeve 24 for receiving a distal end 26 of the endoscope 14 and a distal end 28 of the additional channel 12 in use. The sleeve 24 has a sleeve body 30 defining a sleeve channel 32 therein. The sleeve body 30 has a first open end 34 and a second open end 36. The distal end 26 of the endoscope 14 and the distal end 28 of the additional channel 12 will extend through the sleeve channel 32, between the first and second open ends 34, 36 of the sleeve body 30, in use. The sleeve body 30 has a distal edge 38 and a proximal edge 40 at the first and second open ends 34, 36 respectively. The first open end 34 can also be referred to as a distal end, and the second open end 36 can be referred to as a proximal end. In certain embodiments, the sleeve body 30 has a cylindrical form, although in certain other embodiments, the form of the sleeve body 30 may differ. Sleeve bodies 30 having cross-sectional shapes including tear drop, elliptical, etc., are within the scope of the present disclosure. In the embodiments of FIGS. 1-15, the sleeve body 30 has a one-piece single layer configuration. In the embodiment of FIG. 16, the sleeve body 30 has a wrapped configuration which will be described later with reference to FIGS. 16A and B.

In certain embodiments, a length 42 of the sleeve body 30 (longitudinal dimension between the first and second open ends 34, 36) is more than about 5 mm, and preferably about 10-15 mm. The sleeve 24 is not a "loop" or "lasso" type. The length 42 of the sleeve body 30 is larger than a diameter 44 of the sleeve body 30. In certain embodiments, this provides stability and limits relative movement between two or more of: the sleeve 24, the endoscope 14, and the additional channel 12.

The diameter 44 of the sleeve 24 is fixed in certain embodiments (FIGS. 1-11), or is adjustable in other embodiments (FIGS. 12-16).

The sleeve 24 may be formed of any suitable material which is biocompatible and sterilizable and hence suitable for insertion into the human body. Suitable tensile properties of the material of the sleeve body 30 comprise a tensile strength permitting cohesiveness during the implantation procedure and which can be ruptured using a force to be applied by the user. Examples of sleeve body 30 materials include, but are not limited to, elastomeric materials, such as but not limited to polyurethane, polyether block amide (e.g. PEBAX®), silicone, fluorinated ethylene propylene, polyvinyl chloride, polyester, perfluoroalkoxy alkanes, polypropylene, latex, natural rubber, synthetic rubbers (e.g. polychloroprene such as Neoprene®, perfluoroelastomer such as Kalrez®, nitrile rubber such as Buna®, ethylene propylene diene rubber such as EPDM®, etc).

The attachment system 10 is also provided with a rupture mechanism 46 for rupturing the sleeve body 30 to allow separation of the distal end 28 of the additional channel 12 from the distal end 26 of the endoscope 14. The sleeve 24 can be said to have an intact configuration in which the sleeve body 30 extends around the distal end 26 of the endoscope 14 and the distal end 28 of the additional channel 12, and a ruptured or opened configuration in which the sleeve body 30 is ruptured longitudinally between the first open end 34 and the second open end 36 of the sleeve body 30. It can be said that the sleeve body 30 has a planar configuration once ruptured. By rupture is meant tear, cut, split, ripped, unrolled, etc. The rupture mechanism 46 can be deployed proximally to the sleeve 24 and from outside of the patient, in use.

In certain embodiments, the sleeve body 30 has a tether 48 which can be manipulated proximally from the sleeve body 30 and from outside the patient, in use, such that once the sleeve body 30 is ruptured, the sleeve 24 can be moved away from the site. In some embodiments, the sleeve 24 is removed completely out of the patient after its rupture. In other embodiments, if the patient is connected to a respirator, the sleeve 24 is moved out of the patient and into tubing of the respirator by pulling on the tether 48. This can avoid the sleeve 24 becoming entangled with the additional channel 12 or the endoscope 14. Moving the sleeve 24 away from the site after its rupture can also avoid obstructing a line of sight of a camera of the endoscope 12 or of the additional channel 12.

In certain other embodiments, the sleeve body 30 is attached to one or more of: the endoscope 14, the additional channel 12 and the rupture mechanism 46. The sleeve body 30 remains attached after its rupture. The attachment of the sleeve body 30 to one or more of the endoscope 14, the additional channel 12 and the rupture mechanism 46 may be by any means such as adhesive, a tether, or the like. In this way, the sleeve 24 can be removed from the target position in the patient together with the endoscope 14 or with the additional channel 12.

Various embodiments of the rupture mechanism 46 are contemplated and are described below.

The attachment system 10 also includes a tensioning mechanism 50 in certain embodiments and in combination with any of the various rupture mechanisms 46. Various embodiments of the tensioning mechanisms 50 are also described below.

RUPTURE MECHANISMS

Snare Mechanism

With reference to FIGS. 1-7, in certain embodiments, the rupture mechanism 46 is a snare mechanism 52, deployment of which can rupture the sleeve body 30 to allow separation of the endoscope 14 and the additional channel 12 and to release one or both from the sleeve channel 22. The snare mechanism 52 is connected at a first end 54 to the sleeve body 30, extends proximally from the sleeve 24, and can be deployed at a second end 56 by the user. In certain embodiments, the second end 56 of the snare mechanism 52 is a cord which extends outside of the patient in use for independent manipulation by the user. In other embodiments, the second end 56 may be incorporated into a handle of the endoscope (not shown). The first end 54 of the snare mechanism 52 is a loop of material extending around the sleeve body 30, through the first and second open ends 34, 36 of the sleeve 24 (best seen in FIGS. 1, 2, 4 and 6). The first end 54 is also referred to herein as the looped portion, and the second end 56 as the tail portion. The sleeve body 30 may include one or more frangible portions 58 for facilitating the rupture of the sleeve body 30 when the rupture mechanism 46 is deployed.

In certain embodiments, illustrated in FIGS. 1-4, and 6, the frangible portion 58 comprises a single row of perforations 60. One or more slits 62 may be provided at the distal edge 38 or the proximal edge 40 of the sleeve body 30, adjacent the perforations 60, for facilitating the rupture of the sleeve body 30 (FIGS. 4 and 5).

In other embodiments, the frangible portion 58 comprises a double row of perforations 60 (FIGS. 5A, 5B, and 10-13).

In yet other embodiments, the frangible portion 58 comprises a thinned portion of the sleeve body 30 (not shown).
Blade Mechanism In certain embodiments, the rupture mechanism 46 comprises a blade mechanism 64 arranged to cut the sleeve body 30 from the first open end 34 to the second open end 36 when relative movement is imparted between the sleeve body 30 and the blade mechanism 64 (best seen in FIGS. 8 and 9).

The blade mechanism 64 comprises a blade mechanism body 66 which can be hooked over the distal edge 38 or the proximal edge 40 of the sleeve body 30. The blade mechanism body 66 comprises a first arm 68, a second arm 70 and a blade 72 positioned between the first arm 68 and the second arm 70. The first and second arms 68, 70 may be substantially parallel to one another. In use, at least a portion of the first arm 68 extends along an outside 74 of the sleeve body 30, and at least a portion of the second arm 70 extends along an inside 76 of the sleeve body 30. The blade 72 rests against the distal or proximal edge 38, 40 of the sleeve body 30, and once the blade mechanism 64 is deployed, it is arranged to cut the sleeve body 30. Deployment of the blade mechanism 64 comprises relative movement between the blade mechanism body 64 and the sleeve body 30. Accordingly, the blade mechanism 64 includes a leash 78, associated either with the sleeve 24 or with the blade mechanism body 66 to effect the relative movement.

Figure 8:
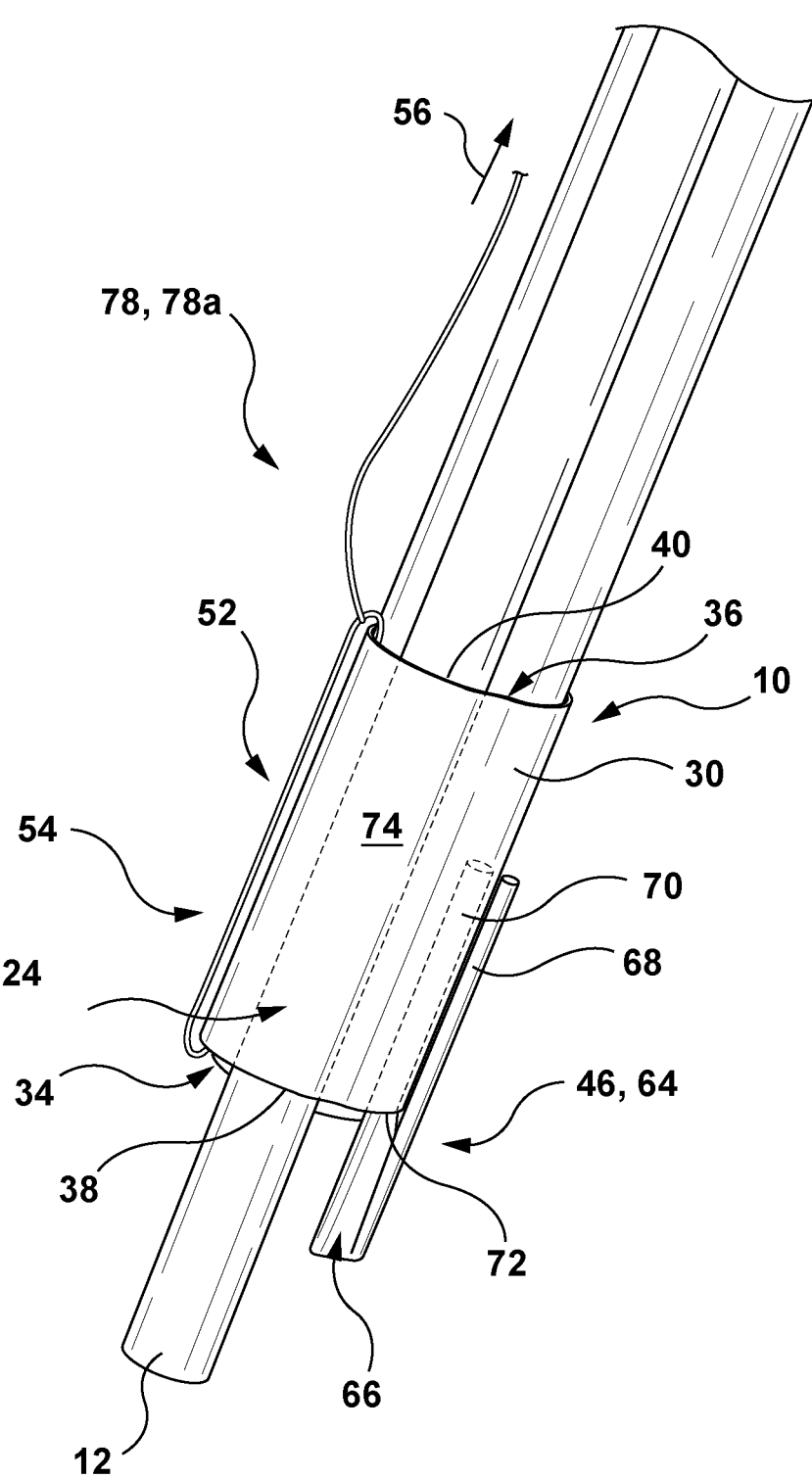
FIG. 8 is a perspective view from the side of another embodiment of an attachment system comprising a sleeve and a rupture mechanism which is a blade mechanism; according to certain embodiments of the present technology.

In the embodiment illustrated in FIG. 8, the leash 78 is associated with the sleeve 24 and is referred to herein as a "sleeve leash" 78a. The sleeve leash 78a is arranged to effect movement of the sleeve body 30 relative to the blade 72 which causes the blade mechanism 64 to cut the sleeve body 30. The sleeve leash 78a may comprise a snare mechanism, similar to the snare mechanism 52 illustrated in FIGS. 1-4, and 6, having the looped portion at the first end 54 which loops through the sleeve body 30, and the tail portion at the second end 56 extending proximally from the sleeve 24 and deployable by the user. In certain embodiments, the second end 56 is a cord which extends outside of the patient in use for independent manipulation by the user. In other embodiments, the second end 56 may be incorporated into a handle of the endoscope (not shown). Pulling the second end 56 of the sleeve leash 78a away from the first open end 34 of the sleeve body 30 causes the relative movement of the sleeve body 30 and the blade 72. In this case, the blade mechanism body 66 is in a fixed relationship relative to the distal end 26 of the endoscope 14 or the distal end 28 of the additional channel 12.

Figure 9:
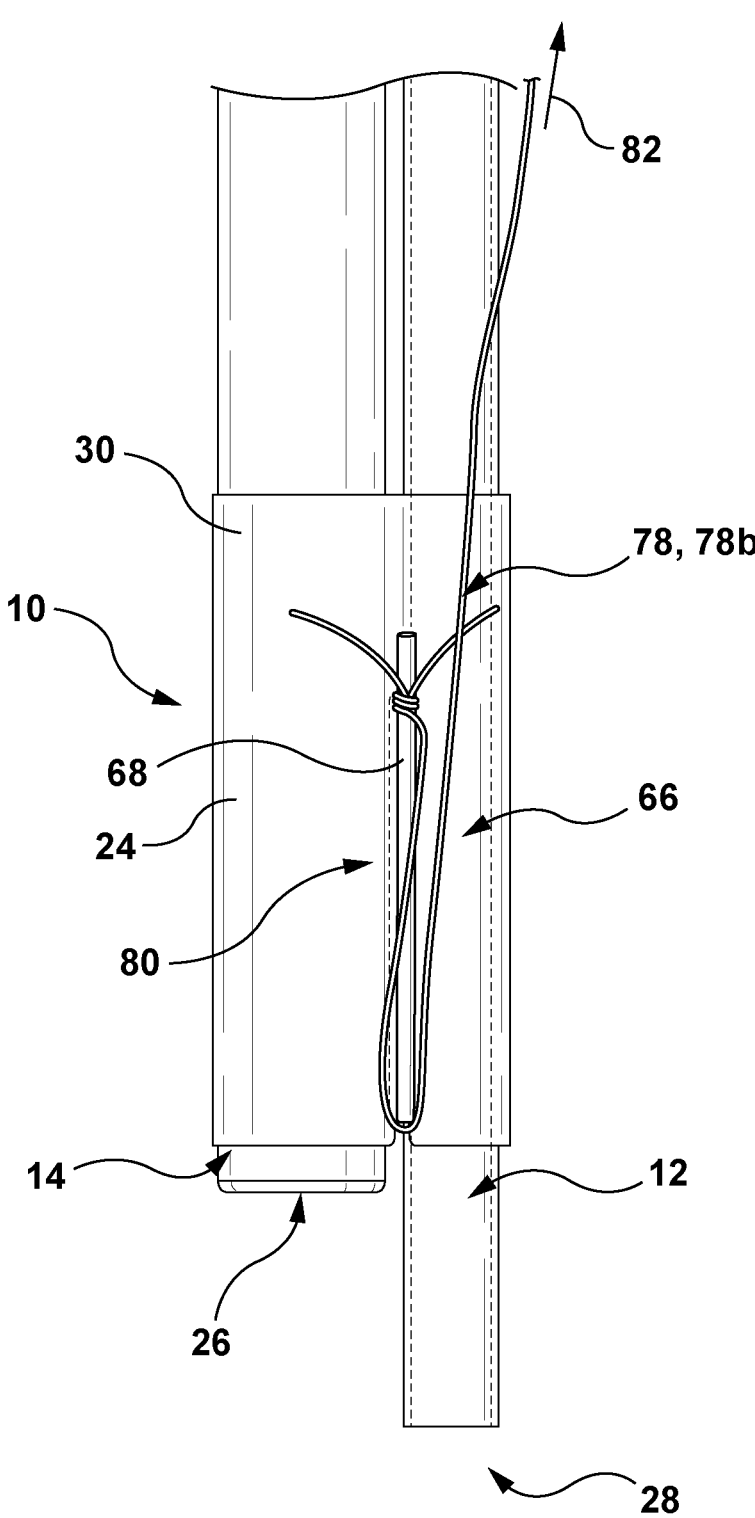
FIG. 9 is a perspective view from the top of an alternative attachment system comprising a sleeve and a rupture mechanism which is a blade mechanism; according to certain other embodiments of the present technology.
Figure 10:
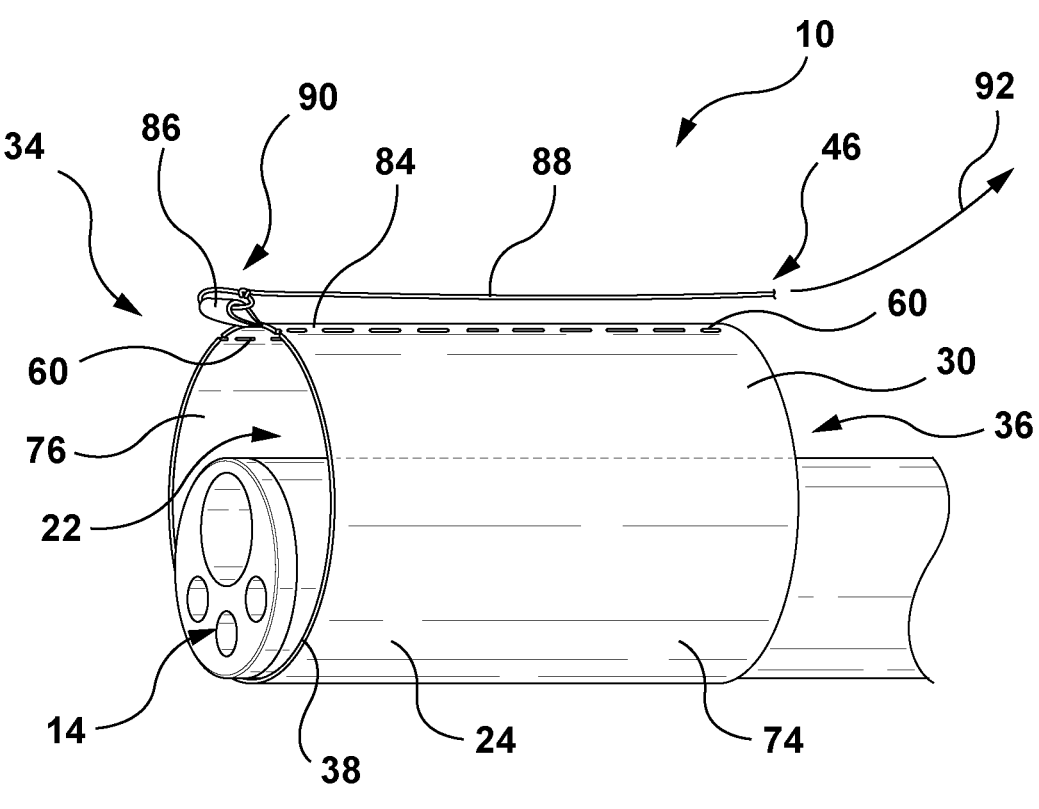
FIG. 10 is a perspective view from the side of an attachment mechanism comprising a sleeve and a rupture mechanism including a removeable strip, according to certain other embodiments of the present technology.
Figure 11:
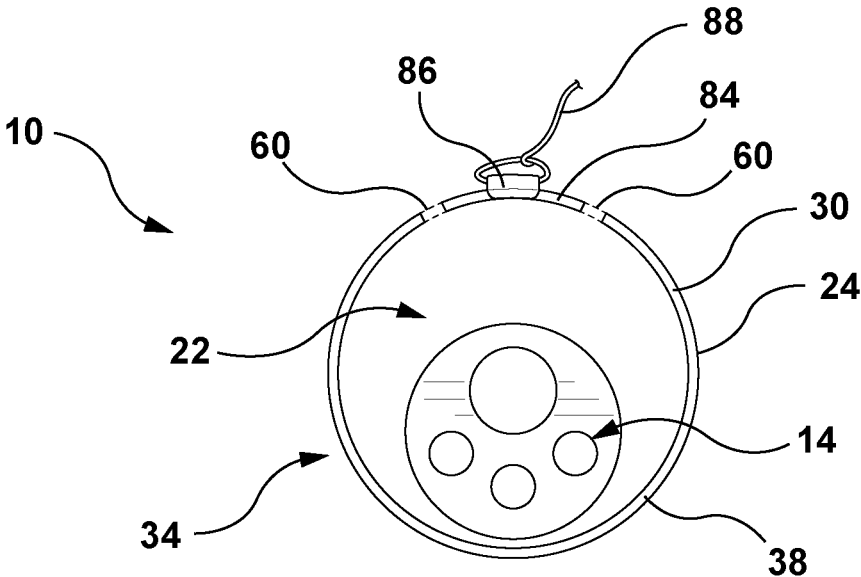
FIG. 11 is an end view of the attachment mechanism of FIG. 10, according to certain other embodiments of the present technology.
Figures 12, 13, 14:
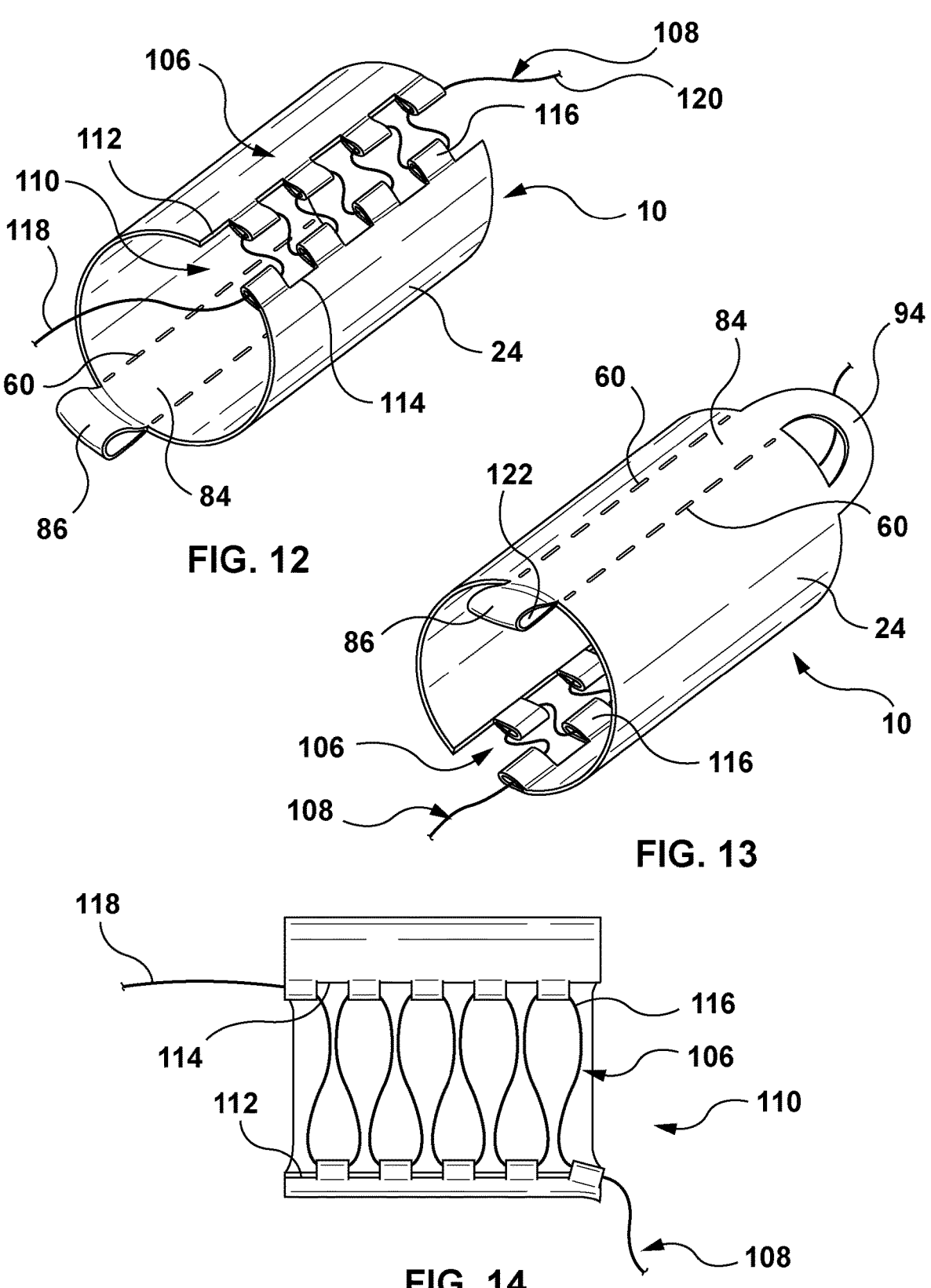
FIG. 12 is a perspective view from the top of the attachment mechanism of FIG. 10 and including a tensioning mechanism, according to certain embodiments of the present technology.
FIG. 13 is a perspective view from the bottom of the attachment mechanism of FIG. 12, according to certain embodiments of the present technology.
FIG. 14 is a close-up view of the tensioning mechanism of FIG. 12, according to certain embodiments of the present technology.
Figure 15A:
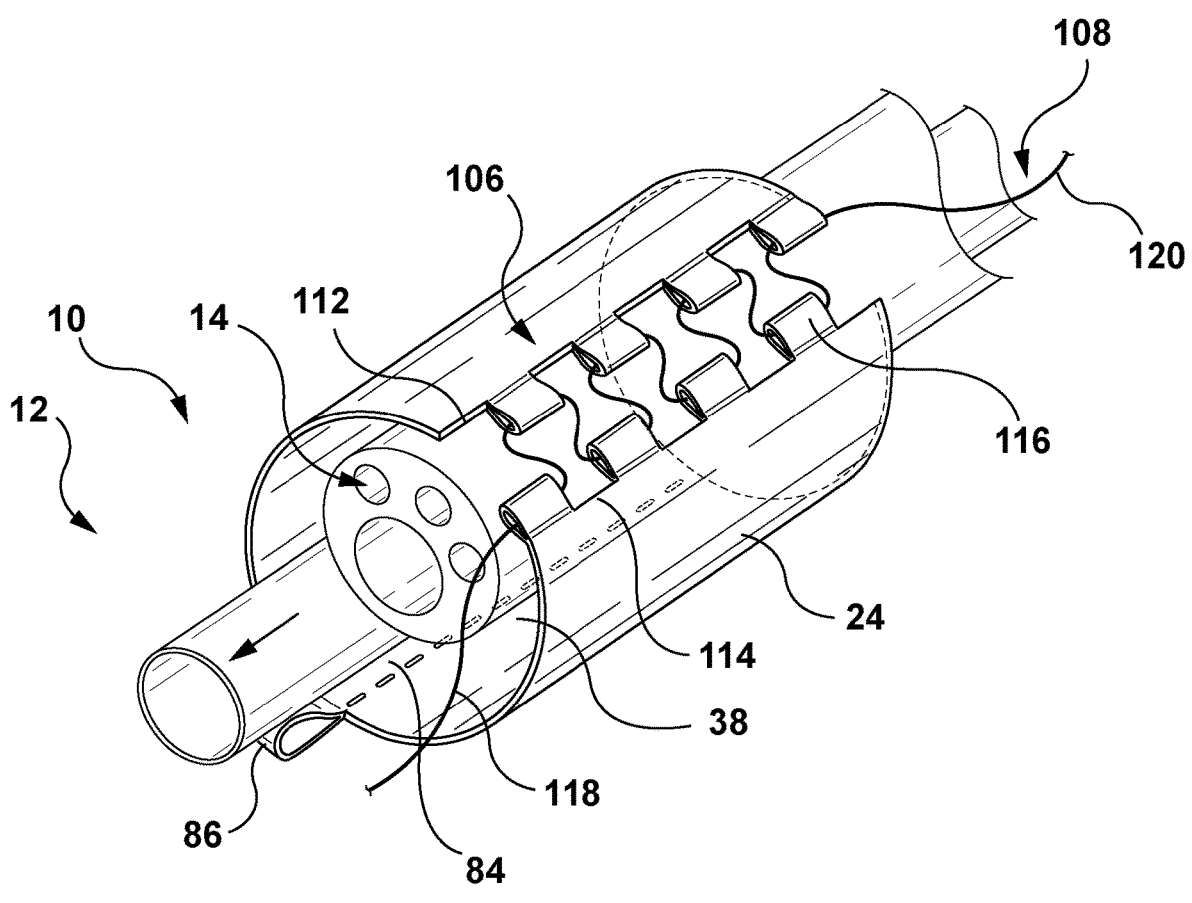
FIG. 15A is a perspective view of an alternative attachment system to that of FIGS. 12-15, according to certain embodiments of the present technology.
Figure 15B:
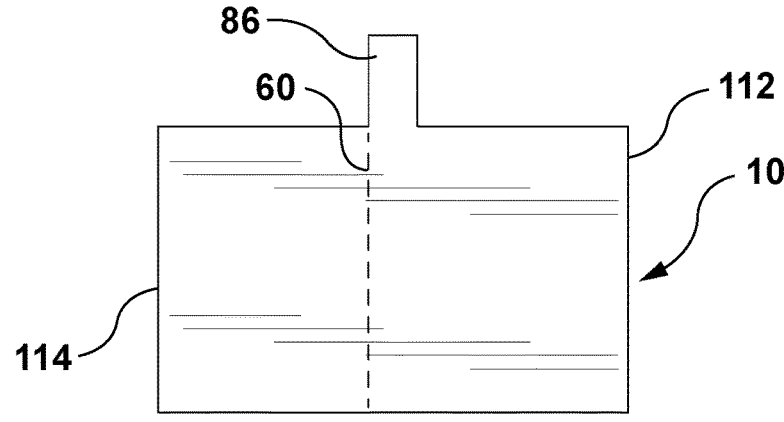
FIG. 15B is a plan view of the sleeve of FIG. 15A when opened up, according to certain embodiments of the present technology.

The embodiment of FIG. 9 differs from that of FIG. 8 in that the leash 78 is associated with the blade mechanism body 66 instead of with the sleeve 24, and is referred to herein as a "blade leash" 78*b*. The blade leash 78*b* has a first end 80 which is connected to the blade mechanism body 66, and a second end 82 which extends proximally to the sleeve 24 and is deployable at the second end 82 by the user, such as through a handle of the endoscope (not shown). Pulling the second end 82 of the blade leash 78*b* causes the relative movement of the sleeve body 30 and the blade 72. In this case, the sleeve body 30 is in a fixed relationship relative to the distal end 26 of the endoscope 14 or the distal end 28 of the additional channel 12.

In a further embodiment, the sleeve leash 78*a* is attached at its first end to the sleeve 24, as before, and at its second end to the blade mechanism body 66 or to the blade leash 78*b*. The sleeve leash 78*a* and the blade leash 78*b* may have a common second end such that pulling on the common second end deploys both the blade mechanism 64 and the snare mechanism 52.

Removable Strip

Referring now FIGS. 10-13 in which is illustrated the rupture mechanism 46 comprising a removeable strip 84. The removeable strip 84 comprises a portion of the sleeve body 30 which is removeable. One or more removeable strips 84 may be provided. The removeable strip 84 comprises two lines of perforations 60 defined in the sleeve body 30, defining two frangible lines, which extend longitudinally along the sleeve body 30 between the first and second open ends 34, 36. Rupture along the two lines of perforations 60 allows removal of the removeable strip 84, and hence opening of the sleeve body 30 to the ruptured configuration, to allow separation of the contents of the sleeve channel 22. The removeable strip 84 is also referred to herein as a "pull tab".

A tab 86 is provided at one end of the removeable strip 84. In certain embodiments, the tab 86 extends from the distal edge 38 of the sleeve body 30. A tab leash 88 is attached to the tab 86 for applying tension to remove the removeable strip 84. The tab leash 88 has a first end 90 which is attached to the tab 86, and a second end 92 extending proximally from the sleeve body 30 and which can be pulled by the user of the attachment system 10 (such as through the endoscope handle) to tear the perforations 60 and remove the removeable strip 84. The tab 86 and a portion of the sleeve body 30 not including the tab 86 may be a single piece.

A tether 94 (FIG. 13) is provided at the other end of the removeable strip 84 for tethering the removeable strip 84 to the sleeve 30. By means of the tether 94, when the perforated lines 60 have been ruptured to detach the removeable strip 84, and the sleeve body 30 actuated into the ruptured configuration, the removeable strip 84 remains attached to the sleeve body 30.

It will be appreciated that the removeable strip 84 may differ from that illustrated in that the two lines of perforations 60 may not necessarily be parallel to one another. They may be linear or non-linear.

In other embodiments, instead of two lines of perforations 60, there is provided a single line of perforations 60 together with the tab 86 and the tab leash 88. Pulling on the tab 86 causes the sleeve 30 to rupture along the single line of perforations 60.

Other rupture mechanisms 46, not illustrated, are also within the remit of the present technology, such as using the snare mechanism 52 to rupture the sleeve body 30 through the single line of perforations 60 or the double line of perforations 60.

TENSIONING MECHANISMS

The attachment system 10, in certain embodiments, also comprises the tensioning mechanism 50. The tensioning mechanism 50 can serve one or more of the following functions: (1) for providing a tension on the sleeve body 30 during actuation of the rupture mechanism 46 or during the rupture itself; (2) for adapting a cross-sectional surface area/diameter 44 of the sleeve body 30 to accommodate different endoscope 14 and/or additional channel 12 diameters (i.e. allowing the sleeve body 30 to have a "one-size fits all" function); and (3) to hold the endoscope 14 and the additional channel 12 closely together (before rupture of the sleeve 30) and limit or avoid relative longitudinal movement between the endoscope 14 and the additional channel 12). In certain embodiments, the tensioning mechanism 50 is put into place during assembly of the attachment system 10 with the endoscope 14 and the additional channel 12 (as opposed to during the in situ positioning of the attachment system 10).

Pin

In certain embodiments, the tensioning mechanism 50 comprises at least one pin 98 having a hook portion 100 and a hook arm 102, wherein the at least one pin 98 is insertable into the sleeve 30 with the hook portion 100 extending over a distal edge 38 of the sleeve body 30 and the hook arm 102 extending longitudinally along the outside 74 the sleeve body 30. Once in position, the contact of the hook arm 102 with the sleeve body 30 provides tension to the sleeve body 30 to facilitate rupturing of the sleeve body 30.

Figure 6:
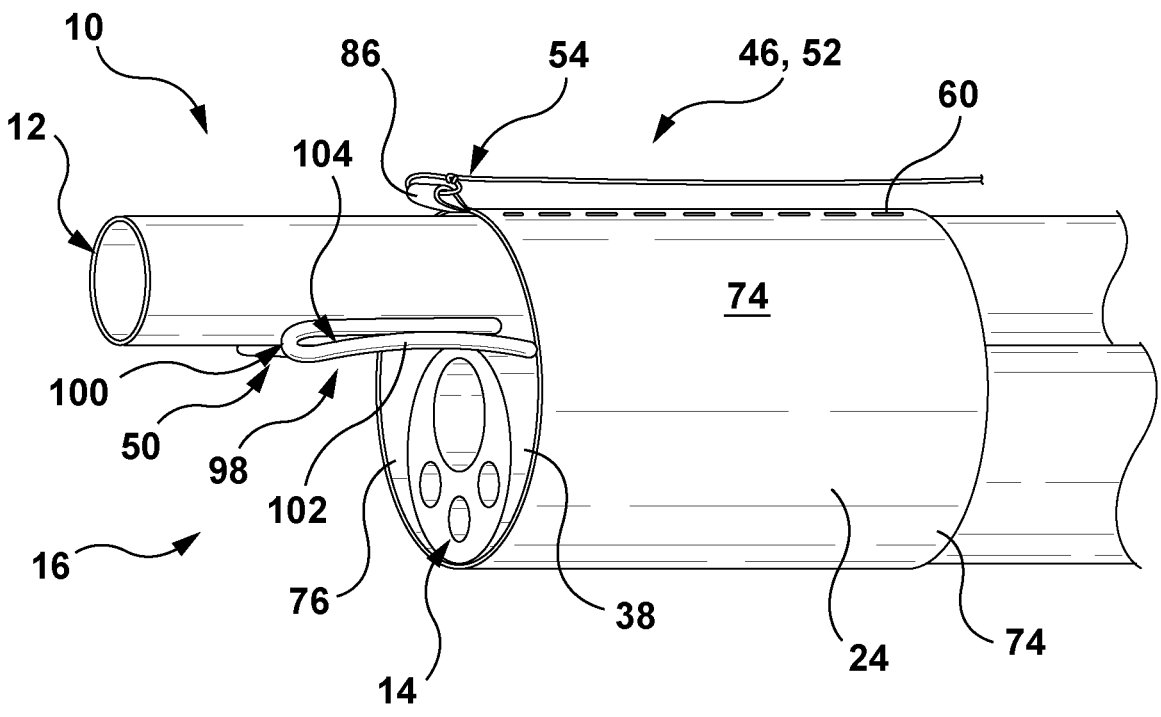
FIG. 6 is a perspective view from the side of an alternative embodiment of the attachment system of FIG. 1 and including a tensioning mechanism in a first position; according to certain embodiments of the present technology.
Figure 7:
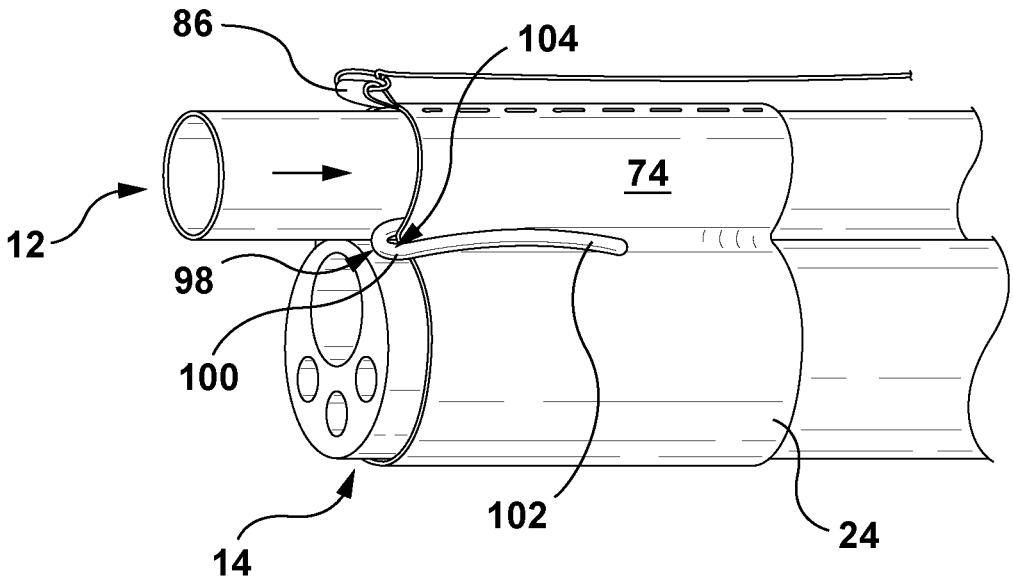
FIG. 7 is the attachment system of FIG. 6, with the tensioning mechanism in a second position; according to certain embodiments of the present technology.

Two pins 98 are provided in the embodiment of FIGS. 6 and 7 in which the rupture mechanism 46 comprises the snare mechanism 52 and the sleeve body 30 includes the row of perforations 60. The two pins 98 are attached to the distal end 28 of the additional channel 12 and circumferentially spaced from one another (FIG. 6). An open jaw 104 of the hook portion 100 faces the distal edge 38 of the sleeve body 30. In use, the additional channel 12 is pulled proximally to cause the hook portion 100 of each pin 98 to engage with the sleeve body 30 (FIG. 7). As can be seen, the two pins 98 are positioned such that they are one on either side of the line of perforations 60 and once they are mated with the sleeve 24, they create tension on the sleeve body 30 around the line of perforations 60 to facilitate the rupture of the perforations 60 using the snare mechanism 52. The pins 98 may be made of metal or any other suitable material.

An additional function of the pins 98, in certain embodiments, is to prevent or limit relative movement between the endoscope 14 and the additional channel 12 by tightening the sleeve 24. In this respect, in certain embodiments, the two pins 98 may be considered as a pair of "wings" on the sleeve 24, once assembled, such that the pins 98 cinch the sleeve 24 to prevent the additional channel 12 from moving with respect to the endoscope 14. By means of avoiding or limiting relative movement of the additional channel 12 and the endoscope 14, a consistent view of the distal end 26 of the endoscope 14 is achieved (relative movement between the additional channel 12 and the endoscope 14 causes the view of devices inside the lung to change).

In other embodiments (not shown) the pin 98 can be provided at the second end 36 of the sleeve body 30 such that the hook portion 100 extends over the proximal edge 40 of the sleeve body 30 in use.

In certain embodiments, the pin 98 is attached to the distal end 26 of the endoscope 14 instead of the additional channel 12. The pin 98 can be attached to the endoscope 14 either directly, or by means of a clip (not shown).

Although the pin 98 embodiment of the tensioning mechanism 96 is illustrated in combination with the snare mechanism 52, this embodiment of the tensioning mechanism 50 can be used with other embodiments of the rupture mechanism 46.

Adjustable Portion of the Sleeve Body

Turning now to FIGS. 12-14, and 16A and 16B, in certain embodiments, the tensioning mechanism 50 comprises an adjustable portion 106 on the sleeve body 30. The adjustable portion 106 can be actuated to adapt a cross-sectional area of the sleeve body 30. Although the adjustable portion 106 embodiment is illustrated in combination with the removeable strip 84 rupture mechanism 46, this embodiment of the tensioning mechanism 50 can be used with other embodiments of the rupture mechanism 46. The adjustable portion 106 extends longitudinally along the sleeve body 30 and comprises a thread 108 extending back and forth through the sleeve body 30 which can be pulled to make the cross-sectional area of the sleeve 24 smaller. The adjustable portion 106 is similar to a corset arrangement.

The sleeve body 30 has a longitudinal split 110 defined by a first slit edge 112 and a second slit edge 114. The first and second slit edges 112, 114 are held together by the thread 108 extending back and forth between the first and second slit edges 112, 114. Loops 116 can be provided on both the first slit edge 112 and the second slit edge 114 through which the thread 108 can extend. The loops 116 may be arranged in an interdigitated configuration. The thread 108 extends alternately through loop 116 on either side of the longitudinal split 110. A first end 118 of the thread 108 extends from the first end 34 of the sleeve body 30 and a second end 120 of the thread 108 extends from the second end 36 of the sleeve body 30. Pulling both the first end and the second end 118, 120 of the thread 108 brings the first slit edge 112 and second slit edge 114 closer together to narrow the longitudinal slit 110 and to decrease a cross-sectional surface area of the sleeve body 30.

In other embodiments (not shown), the sleeve body 30 may be a single cylindrical piece (similar to that illustrated in FIG. 10) and including the thread 108 and optionally the loops 116.

In certain embodiments, one or more of the loops 116 have an interior surface 122 which provides sufficient friction to retain the thread 108 in the pulled position. In other embodiments, the thread 108 may be knotted through the loop 116 to attach the thread 108 to the loop 116.

This embodiment of the tensioning mechanism 50 can also be used to adjust the cross-sectional area of the sleeve body 30 in order to accommodate different sizes and shapes of the endoscope 14 and the additional channel 12. In this way, the attachment system 10 can provide a "one-size fits all" system that can be retrofit to a large combination of endoscopes 14 and additional channels 12. With such uses, the thread 108 is pulled to the appropriate tension and can be knotted to secure the position before delivery to the patient. In certain aspects of the present disclosure, the sleeve 24 may be provided with the tensioning mechanism 50 in the absence of the rupture mechanism 46. The tensioning mechanism 50 also functions to limit or avoid relative movement between the endoscope 14 and the additional channel 12 within the sleeve 24 in use. By relative movement is meant one or more of a relative longitudinal movement and a radial movement. As mentioned earlier, this can help to keep the view of devices from the video feed consistent. The attachment system 10 of FIGS. 15A and 15B differs from that of FIGS. 12 and 13, in that a single line of perforations 60 is provided on the sleeve 24 and the tether

94 is omitted. Pulling the tab 86 causes rupture of the sleeve 24 along the single line of perforations 60.

Wrapped Configuration

Turning now to FIGS. 16A and 16B in which there is shown certain embodiments of the attachment system 10 in which the sleeve body 30 has a wrapped configuration, instead of the single layer configuration of FIGS. 1-15. In the wrapped configuration, the sleeve body 30 is a planar piece of material with two free longitudinal ends 124 and having a support pin 126 attached to the planar sleeve body 30. A tether 128 is attached to the support pin 126. In use, the planar sleeve body 30 is wrapped around the endoscope 14 and the additional channel 12 before delivering to the target site in the patient. Pulling the tether 128, causes the sleeve body 30 to unravel to allow separation of the endoscope 14 and the additional channel 12.

Anti-Rotation Device

Figure 17A:
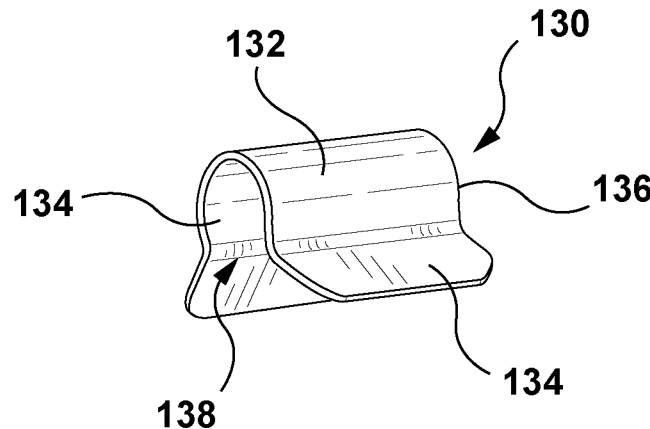
FIG. 17A is a perspective view of a wing clip for use with an attachment system, according to certain embodiments of the present technology.
Figure 17B:
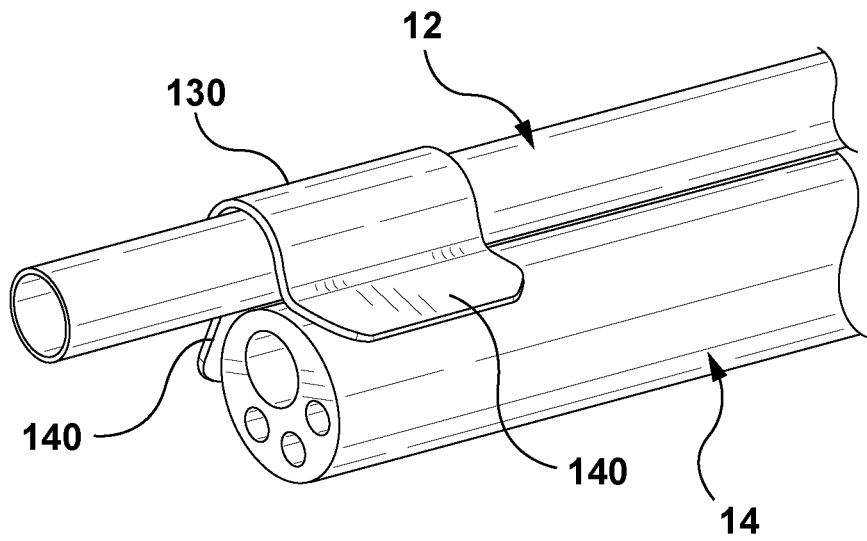
FIG. 17B is a perspective view of the wing clip of FIG. 17A attached to an additional channel and assembled with an endoscope, according to certain embodiments of the present technology.

Turning now to FIGS. 17A and 17B, there is shown certain embodiments of an anti-rotation device that can be used with any of the embodiments of the attachment systems 10 described herein to prevent or limit an undesired relative movement of the additional channel 12 and the endoscope 14. In certain embodiments, the undesired relative movement is a relative rotation of the additional channel 12 and the endoscope 14.

As illustrated in FIGS. 17A and 17B, the anti-rotation device comprises a wing clip 130. The wing clip 130 comprises a u-shaped body 132 defining a channel for receiving the additional channel 12. The u-shaped body wraps at least partially around a periphery of the additional channel 12. The body 132 has two open ends 134, 136 and an open side 138 through which the additional channel 12 can be clipped by the wing clip 130. A pair of wings 140 extend from the edges of the open side and flare outwardly, in a mirror image configuration. In use when the additional channel 12 is assembled with the endoscope 14 (FIG. 17B), the wings 140 rest against the endoscope 14, and prevent or limit rotational movement of the additional channel 12 relative to the endoscope 14. The wing clip 130 may be formed by thermoforming a plastic material.

In certain other embodiments, the anti-rotation device may be configured differently to the wing-clip 130. For example, instead of the anti-rotation device being removably attachable to the additional channel 12, the anti-rotation device may be configured to be attached to the outer surface of the additional channel 12. In these embodiments, the anti-rotation device may comprise wedge-like protrusions that extend outwardly from the outer surface of the additional channel 12.

It will be appreciated that the attachment system 10 can be suitable for use with any type of endoscope 14, such as a bronchoscope. The bronchoscope may have a working channel permitting one or more of: visualization and suction. The attachment system 10 may be used as a retrofit to an existing endoscope 14, in which case the endoscope 14, the additional channel 12 and the attachment system 10 may be assembled before delivery to the target tissue site of the patient.

The additional channel 12 may comprise a single or a plurality of additional channels. The additional channel 12, in certain embodiments, comprises the sheath 20 for housing a guide wire, along which guide wire can be advanced a balloon occlusion device and/or a biopsy device. The additional channel 12 may further comprise a steering cable for independent positioning of the additional channel 12 to the endoscope 14. The additional channel 12 can comprise the sheath 20 sized and shaped to house a guide wire and permit movement of one or more of a balloon occlusion device, and a biopsy device, such as a cryobiopsy device, along the guide wire.

Kits

Referring now to FIGS. 18-21, in certain aspects, the attachment system 10 is provided as a kit 150, the kit 150 comprising one or more of the following components:

the attachment system 10 (sleeve 24, rupture mechanism 46, and optionally the tensioning mechanism 50), the additional channel 12, a cryoprobe (such as the cryoprobe 166 in FIGS. 19A-C, 20, 21) for insertion into the additional channel 12, a gas delivery assembly for cooling the cryoprobe, one or more balloons (such as the balloon 194 in FIG. 20) for bleeding control, and one or more anti-rotation devices, such as the wing clip 130.

Figure 18:
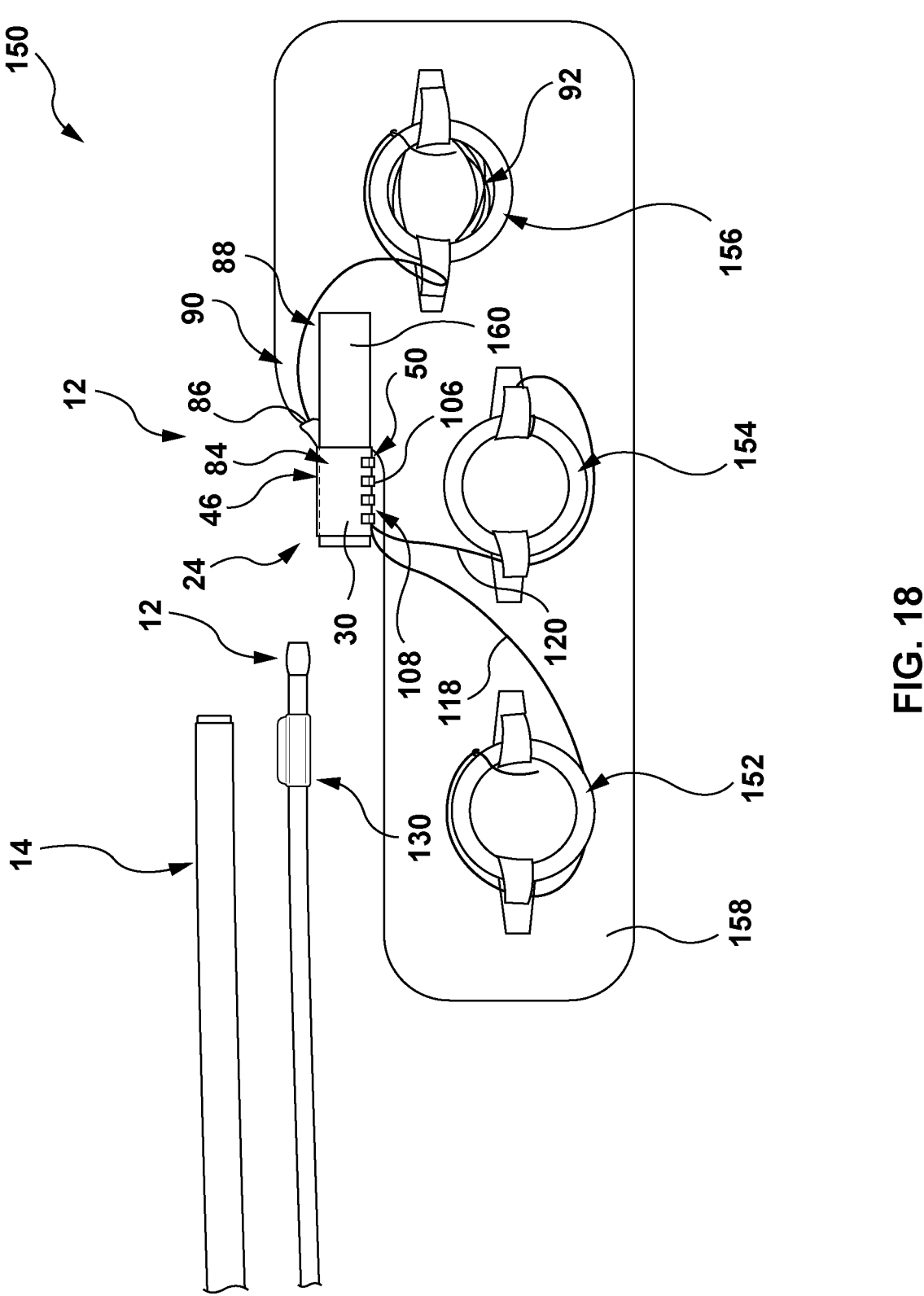
FIG. 18 is plan view of a kit including the attachment system of FIG. 12, according to certain embodiments of the present technology.

One embodiment of a kit 150 according to the present technology is depicted, at least partially, in FIGS. 18-21. As best seen in FIG. 18, the sleeve 24 includes the tensioning mechanism 50 of FIGS. 12-14, and 16A-B including the corset-like adjustable portion 106 on the sleeve body 30 with the thread 108 extending therethrough and having the first end 118 and the second end 120 of the thread 108 extending from opposite ends of the sleeve body 30. The sleeve 24 also includes the removeable strip 84 with the tab 86 provided at one end. Attached to the tab 86 is the first end 90 of the tab leash 88. Pulling on the second end 92 of the tab leash 88 applies tension to remove the removeable strip 84.

First and second rings 152, 154 are provided which are attached to the first and second ends 118, 120 of the thread 108 respectively. A third ring 156 is provided which is attached to the second end 92 of the tab leash 88. The first, second and third rings 152, 154, 156 are removably attached to a support 158 of the kit 150. The sleeve 24 is also attached to the support 158 via a tubing 160 to which the sleeve 24 is detachably mounted. The attachment of any one or more of the first, second and third rings 152, 154, 156 and the tubing 160 to the support 158 can be by adhesive, sticky tape, Velcro™, or the like.

As can be seen in FIG. 18, the kit 150 may also include the additional channel 12 (the distal end of which is shown in FIG. 18), which in the embodiment of FIG. 18 is provided with the wing clip 130 as an anti-rotation device for preventing or limiting rotational movement of the additional channel 12 relative to the endoscope 14. FIG. 18 also shows a distal end of the endoscope 14. However it will be appreciated that the endoscope 14 may not form part of the kit 150 in certain embodiments.

Assembly of these components of the kit 150 comprises inserting the distal end of the endoscope 14 into the tubing 160 and sliding the sleeve 24 off the tubing 160 and over the endoscope 14 distal end. The additional channel 12 is then slid into the sleeve 24 adjacent the endoscope 14 distal end. The wing clip 130 prevents or limits the rolling of the additional channel 12 against the endoscope 14 during assembly and use. The sleeve 24 has a loose configuration at this stage in that the thread 108 has not been pulled to tighten the sleeve 24. The first and second rings 152, 154 are then removed from the support 158 and pulled to tighten the sleeve 24 around the endoscope 14 and the additional channel 12. At this point, when a desired tension has been applied, the first and second ends 118, 120 of the thread 108 can be knotted and the first and second rings 152, 154 can be removed, such as by cutting. The third ring 156 is kept attached to the tab leash 88 until use on the patient, when it can be pulled to break the frangible link and remove the sleeve 24.

Cryoprobe

Figure 19A:
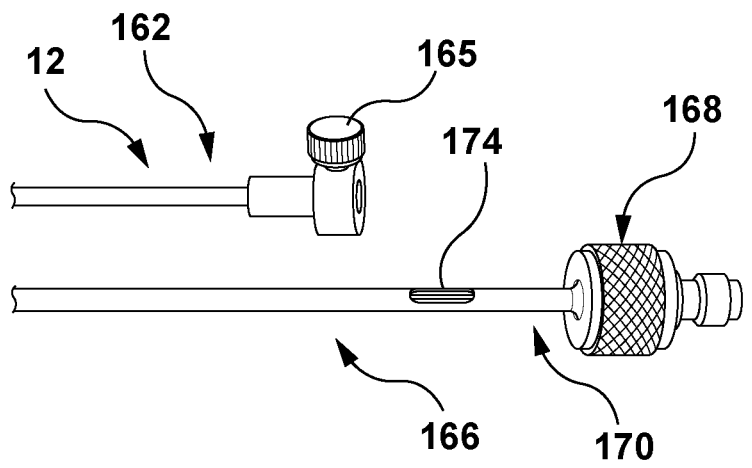
FIGS. 19A and B are perspective views from a proximal end of an additional channel and a cryoprobe, shown disassembled (FIG. 19A) and assembled (FIG. 19B), which may be part of the kit of FIG. 18, according to certain embodiments of the present technology.
Figure 19B:
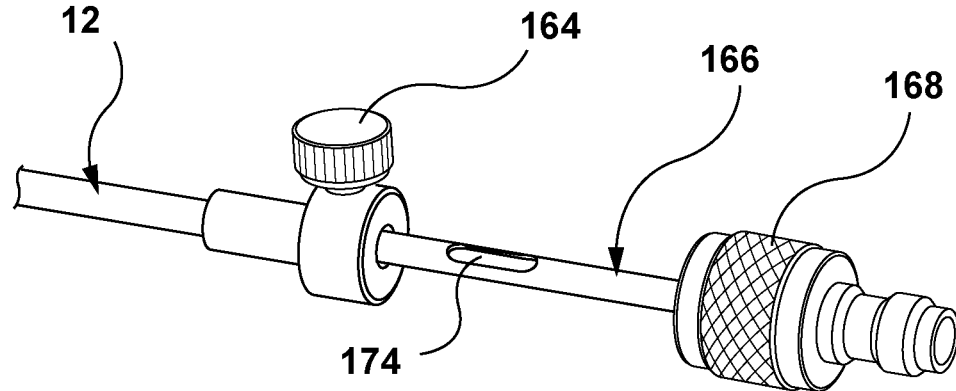
FIG. 19C is a close-up view of the assembled additional channel and cryoprobe of FIG. 16B, according to certain embodiments of the present technology.
Figure 19C:
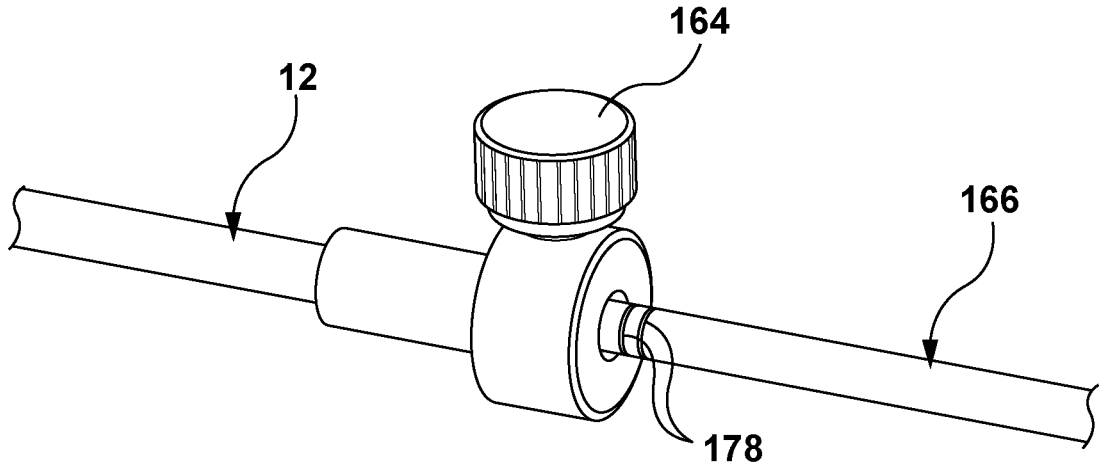

FIGS. 19A-C depict a proximal end 162 of the additional channel 12. At the proximal end 162 there is provided a securing mechanism for securing an insert within the sleeve channel 22 of the additional channel 12. In the illustrated embodiment, the insert comprises a cryoprobe 166, but may also be any other type of insert. The securing mechanism comprises a set screw 164 that can be advanced into the sleeve channel 22 to contact the insert 166 and secure it in place. In other embodiments, the securing mechanism may be any other type of securing mechanism such as a screw, a bolt, a clamp or the like.

The cryoprobe 166 is sized and shaped to be received in the additional channel 12 and has a connector 168 at its proximal end 170 which is configured to be removably attachable to a cooling assembly (not shown). An exhaust opening 174 is provided distally of the connector 168 for gas exhaust during cryobiopsy. The cryoprobe 166 is configured such that the exhaust opening 174 remains exposed when the cryoprobe 166 and the additional channel 12 are assembled and during use. Markers 178 are provided on the outside of the cryoprobe 166 which indicate an extension distance of a distal end of the cryoprobe 166 from the distal end of the additional channel 12. The markers 178 may be provided to indicate, for example, extensions of one or more of 0 cm (i.e. the distal ends are flush), 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm and 20 cm. The cryoprobe 166 comprises an inner tube (not shown) and an outer tube defining a channel therebetween, and a sealed distal end with a fine tip. The inner tube may be a capillary tube having an inner diameter of any suitable size. For example, in certain embodiments the inner diameter is within a range of about 0.01 cm to about 0.03 cm. In certain embodiments, the inner diameter is about 0.02 cm. In certain embodiments the inner diameter is within a range of about 0.007 inches to about 0.01 inches, 0.008 inches. In certain embodiments, a diameter of the outer tube may be about 0.017 cm to about 0.3 cm, or about 0.066 inches to about 0.118 inches. In certain embodiments, the diameter of the outer tube is 0.066 inches. In certain other embodiments, the diameter of the outer tube is 0.118 inches. The inner tube is co-axial with the outer tube and extends, within the outer tube, from the connector 168 to a distal tip of the cryoprobe 166.

In use, the cooling assembly is configured to cool the distal tip of the cryoprobe 166 for application of freezing and/or cryotherapy to tissues in contact with the distal tip. Without being bound to any theory, the cooling of the distal tip can be attributed to a forcing of gas or liquid by the cooling assembly through the inner tube from high pressure (at the proximal end) to low pressure (at the distal tip), such as may be defined by the Joule-Thomson effect. Expansion of the forced liquid or gas at the distal tip as it exits the inner tube causes the cooling. The gas then travels towards the proximal end of the cryoprobe 166 before exiting through the exhaust opening 174.

Pressurized gas from the cooling assembly is forced through the inner tube of the cryoprobe 166 and is able to rapidly expand and gasify, due to heat transfer from surrounding tissues at the distal tip, causing the cooling. The low pressure gas can then flow upwardly between the inner and outer tubes and be vented through the exhaust opening 174. The cooling assembly can provide control of the cooling through release and pressure of the gas or liquid.

Balloon

Figure 20:
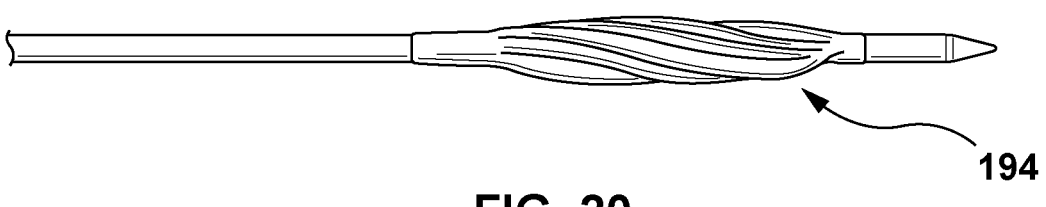
FIG. 20 is a plan view of a balloon, which may form part of the kit of FIG. 18, according to certain embodiments of the present technology.
Figure 21:
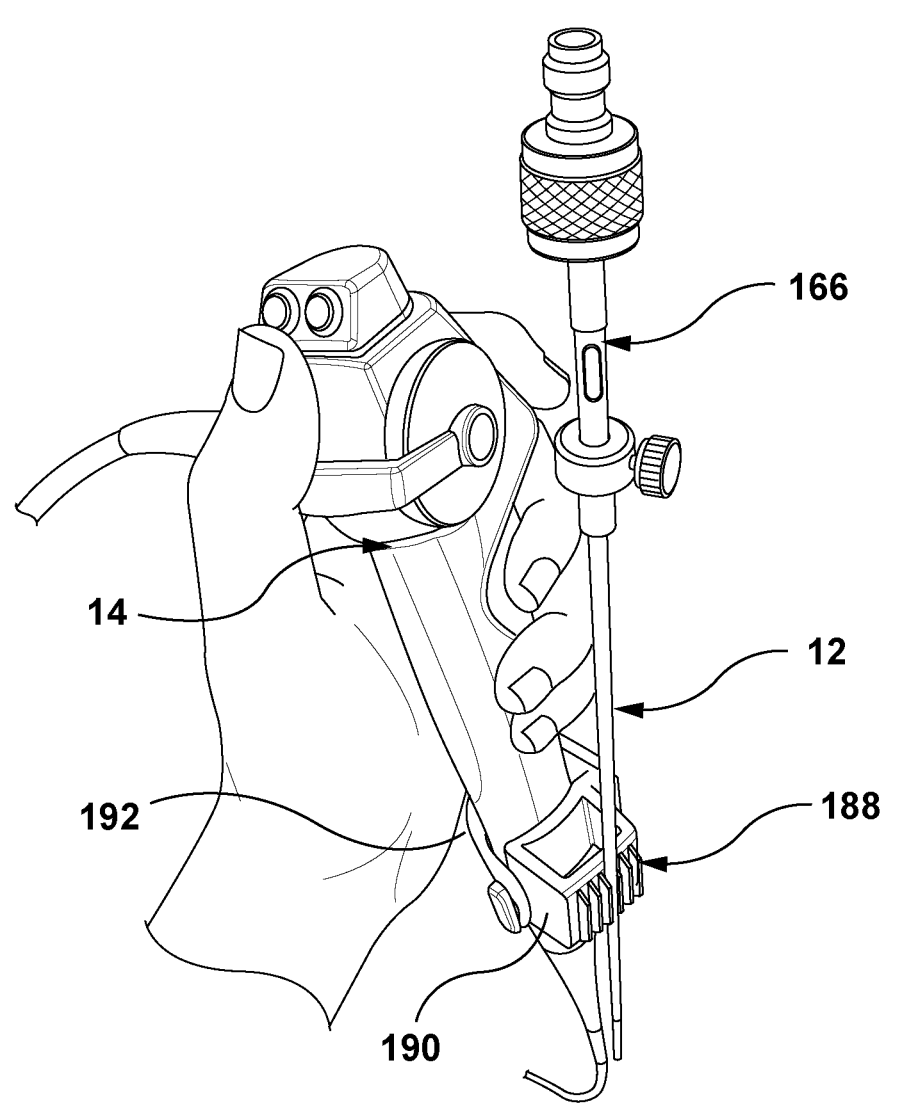
FIG. 21 is a perspective view from a proximal end of the additional channel and cryoprobe of FIGS. 19A and B attached to a bronchoscope, according to certain embodiments of the present technology.

In certain embodiments, the kit 150 is provided with a balloon 194 which can be attached to the distal end of the endoscope 14 or the additional channel 12 for inflation, in use, to stop bleeding for example (FIG. 20). Wing clip Anti-Rotation Devices In certain embodiments, the kit 150 is provided with one or more anti-rotation devices for preventing or limiting an undesired movement of the additional channel 12 relative to the endoscope 14. As noted above and shown in FIG. 18, in certain embodiments, the anti-rotation device is the wing clip 130. The wing clip 130 may be attachable to either the additional channel 12 or the endoscope. In other embodiments, not shown, the anti-rotation device may differ from the wing clip 130 illustrated and described herein. The anti-rotation device may have any suitable configuration for preventing or limiting the undesired movement of the additional channel 12 relative to the endoscope 14, such as a relative rolling or rotation. The anti-rotation device may be removably attachable to either or both of the additional channel 12 and the endoscope 14.

It will be appreciated that any of the above described components of the kit 150 may be provided individually for use with other components not described herein. It will also be appreciated that other embodiments of the kit components may be included in the kit. For example, the kit 150 may include another embodiment of the sleeve 24 such as the one illustrated and described in relation to FIG. 10 or FIG. 15. The kit 150 may include other embodiments of the anti-rotation device. The kit may include the cooling assembly 172 and the cryoprobe.

Methods of Use

In use, the assembly 16 including the attachment system 10, the endoscope 14 and the additional channel 12, is delivered to the target tissue in the patient. At an appropriate time, the rupture mechanism 46 is deployed to separate the endoscope 14 from the additional channel 12. Optionally, the tensioning mechanism 50 can be deployed at that time, if not already applied during assembly of the attachment system 10 to the endoscope 14 and the additional channel 12 during assembly, to facilitate the rupture of the sleeve 24. The endoscope 14 and the additional channel 12 can then be caused to function separately from one another. At the least, this means that one of the endoscope 14 and the additional channel 12 can be removed from the patient whilst the other of the endoscope 14 and the additional channel 12 remains in the patient.

Variations and modifications will occur to those of skill in the art after reviewing this disclosure. The disclosed features may be implemented, in any combination and subcombinations (including multiple dependent combinations and sub-combinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

It should be appreciated that the invention is not limited to the particular embodiments described and illustrated herein but includes all modifications and variations falling within the scope of the invention as defined in the appended claims.

What is claimed is:

1. An attachment system for detachably attaching an additional channel to an endoscope, the attachment system comprising:
a sleeve for receiving a distal end of the endoscope and a distal end of the additional channel in use, the sleeve having:
a sleeve body defining a sleeve channel, through which the distal end of the endoscope and the distal end of the additional channel will extend in use, and having a first open end and a second open end;
a tab connected to the sleeve;
a rupture mechanism for rupturing the sleeve body to allow separation of the distal end of the additional channel from the distal end of the endoscope in situ, the rupture mechanism comprising a leash connected to the tab; and
a mechanism comprising a thread extending through the sleeve body which can be pulled to make a cross-sectional area of the sleeve body smaller.

2. The attachment system of claim 1, further comprising a frangible portion on the sleeve body extending between the first open end and the second open end.

3. The attachment system of claim 1, wherein the leash has a first end and a second end, the first end being connected to the sleeve, wherein pulling the second end of the leash causes at least a portion of the sleeve body to rupture.

4. A kit comprising,
the attachment system of claim 1; and,
the additional channel wherein the additional channel is configured to receive a secondary medical device.

5. The kit of claim 4, further comprising a cryoprobe and wherein the additional channel is sized and shaped to receive the cryoprobe.

6. The attachment system of claim 1, wherein the mechanism comprises a corset arrangement.

7. The attachment system of claim 1, wherein the mechanism extends longitudinally along the sleeve body.

8. The attachment system of claim 7, wherein the sleeve body has a slit extending longitudinally between the first and second open ends of the sleeve body, the slit defined by a first slit edge and a second slit edge, the thread being arranged to bring closer together the first and second slit edges of the sleeve body when actuated.

9. The attachment system of claim 8, further comprising a plurality of loops extending from the first and second slit edges, each loop of the plurality of loops being arranged to receive the thread.

10. The attachment system of claim 1, wherein:
the rupture mechanism comprises a removeable strip defined by two rows of perforations on the sleeve body extending between the first open end and the second open end; and
a tether connecting the removeable strip to the sleeve, the tether being configured to maintain connection between the removable strip and the sleeve after rupture of the rupture mechanism.

11. A method of using an endoscope with an attachment system wherein the endoscope is removably coupled to an additional channel, the method comprising:
pulling a thread of a mechanism of the attachment system to make a cross-sectional area of a sleeve body of the attachment system smaller, wherein the thread extends through the sleeve body; and
deploying a rupture mechanism in situ, wherein the rupture mechanism is configured to rupture a sleeve body of the attachment system, the rupture mechanism comprises a snare mechanism associated with the sleeve body, and deploying the rupture mechanism comprises pulling the snare mechanism to cause at least a portion of the sleeve body to rupture.

12. The method of claim 11, further comprising manipulating the additional channel independently from the endoscope to allow separation of the additional channel.

13. The method of claim 11, wherein pulling the thread is performed during assembly of the attachment system with the endoscope and the additional channel.

14. An attachment system for detachably attaching an additional channel to an endoscope, the attachment system comprising:

a sleeve for receiving an endoscope and an additional channel in use, the sleeve having:

a sleeve body defining a sleeve channel, in which the endoscope and the additional channel will be received in use, and having a first open end and a second open end; and, a rupture mechanism for rupturing the sleeve body to allow separation of the additional channel and the endoscope in situ, the rupture mechanism comprising:

a snare mechanism having a first end attached to the sleeve body, and a second end extending proximally from the first end and arranged to be actuated by a user to cause the sleeve body to rupture.

15. The attachment system of claim 14, further comprising a mechanism for adjusting the sleeve, wherein the mechanism can be actuated to modulate a cross-sectional area of the sleeve.

16. The attachment system of claim 15, wherein the mechanism comprises a corset arrangement.

17. A method of using an endoscope with an attachment system wherein the endoscope is removably coupled to an additional channel, the method comprising:

pulling a thread of a mechanism of the attachment system to make a cross-sectional area of a sleeve body of the attachment system smaller, wherein the thread extends through the sleeve body; and deploying a rupture mechanism in situ, wherein the rupture mechanism is configured to rupture a sleeve body of the attachment system, the rupture mechanism comprising a leash connected to a tab, the tab being connected to the sleeve body, and deploying the rupture mechanism comprises pulling the leash to cause at least a portion of the sleeve body to rupture.

18. The method of claim 17, further comprising continuing to pull the leash to remove the sleeve body.

19. The method of claim 17, further comprising manipulating the additional channel independently from the endoscope to allow separation of the additional channel.

20. The method of claim 17, wherein pulling the thread is performed during assembly of the attachment system with the endoscope and the additional channel.

\* \* \* \* \*